(12) United States Patent
Hogard et al.

(10) Patent No.: US 11,305,040 B2
(45) Date of Patent: Apr. 19, 2022

(54) DIALYSIS SYSTEM AND METHODS

(71) Applicant: OUTSET MEDICAL, INC., San Jose, CA (US)

(72) Inventors: Michael Edward Hogard, Sunnyvale, CA (US); Gopi Lingam, San Jose, CA (US); Dean Hu, San Leandro, CA (US); Balaji M. Maniam, Fremont, CA (US); James Ritson, San Jose, CA (US); Andy H. Uchida, Los Altos, CA (US); John David Stienmier, Arvada, CO (US); Paul David McGregor, Golden, CO (US)

(73) Assignee: Outset Medical, Inc., San Jose, CA (US)

( * ) Notice: Subject to any disclaimer, the term of this patent is extended or adjusted under 35 U.S.C. 154(b) by 0 days.

(21) Appl. No.: 14/821,362

(22) Filed: Aug. 7, 2015

(65) Prior Publication Data

US 2015/0343133 A1 Dec. 3, 2015

Related U.S. Application Data

(63) Continuation of application No. 14/699,875, filed on Apr. 29, 2015, now abandoned.

(Continued)

(51) Int. Cl.
*B01D 19/00* (2006.01)
*A61M 1/16* (2006.01)
*A61M 1/36* (2006.01)

(52) U.S. Cl.
CPC .......... *A61M 1/1621* (2014.02); *A61M 1/166* (2014.02); *A61M 1/1658* (2013.01);

(Continued)

(58) Field of Classification Search
USPC ................................................ 95/24; 96/157
See application file for complete search history.

(56) References Cited

U.S. PATENT DOCUMENTS

| 1,662,870 A | 3/1928 | Stancliffe |
| 3,356,360 A | 12/1967 | Ward |

(Continued)

FOREIGN PATENT DOCUMENTS

| CA | 2887068 A1 | 4/2014 |
| CA | 2930431 A1 | 5/2015 |

(Continued)

OTHER PUBLICATIONS

Miller et al.; U.S. Appl. No. 14/858,876 entitled "Dialysis machine having a conductivity sensor for determining fluid properties," filed Sep. 18, 2015.

(Continued)

*Primary Examiner* — T. Bennett McKenzie
(74) *Attorney, Agent, or Firm* — Shay Glenn LLP

(57) ABSTRACT

Dialysis systems and methods are described which can include a number of features. The dialysis systems described can be to provide dialysis therapy to a patient in the comfort of their own home. The dialysis system can be configured to prepare purified water from a tap water source in real-time that is used for creating a dialysate solution. The dialysis systems described also include features that make it easy for a patient to self-administer therapy. For example, the dialysis systems include disposable cartridge and patient tubing sets that are easily installed on the dialysis system and automatically align the tubing set, sensors, venous drip chamber, and other features with the corresponding components on the dialysis system. Methods of use are also provided, including automated priming sequences, blood return sequences, and dynamic balancing methods for controlling a rate of fluid transfer during different types of (Continued)

dialysis, including hemodialysis, ultrafiltration, and hemodiafiltration.

17 Claims, 17 Drawing Sheets

Related U.S. Application Data

(60) Provisional application No. 61/985,779, filed on Apr. 29, 2014, provisional application No. 62/127,155, filed on Mar. 2, 2015.

(52) U.S. Cl.
CPC ........ *A61M 1/1672* (2014.02); *A61M 1/3643* (2013.01); *A61M 1/3644* (2014.02); *A61M 1/3647* (2014.02); *A61M 1/3649* (2014.02); *A61M 2205/121* (2013.01); *A61M 2205/123* (2013.01); *A61M 2205/14* (2013.01); *A61M 2205/18* (2013.01); *B01D 19/0063* (2013.01); *Y10T 29/49782* (2015.01); *Y10T 29/49897* (2015.01); *Y10T 137/0424* (2015.04)

(56) References Cited

U.S. PATENT DOCUMENTS

| | | | |
|---|---|---|---|
| 3,695,445 A | 10/1972 | Esmond | |
| 3,710,237 A | 1/1973 | Watson et al. | |
| 3,762,032 A | 10/1973 | Bowling et al. | |
| 3,809,309 A | 5/1974 | Batista | |
| 3,827,563 A | 8/1974 | Boe et al. | |
| 3,965,008 A | 6/1976 | Dawson | |
| 4,080,295 A | 3/1978 | Riede | |
| 4,089,456 A | 5/1978 | Toppen et al. | |
| 4,100,068 A | 7/1978 | Jordan et al. | |
| 4,110,220 A | 8/1978 | Lavender | |
| 4,115,273 A | 9/1978 | Winstead | |
| 4,155,157 A | 5/1979 | Gersbacher | |
| 4,172,033 A | 10/1979 | Willock | |
| 4,194,014 A | 3/1980 | Hermans et al. | |
| 4,204,628 A | 5/1980 | Houston et al. | |
| 4,209,391 A | 6/1980 | Lipps | |
| 4,229,299 A | 10/1980 | Savitz et al. | |
| 4,231,366 A * | 11/1980 | Schael | A61M 1/30 128/DIG. 13 |
| 4,267,040 A | 5/1981 | Schal | |
| 4,293,409 A | 10/1981 | Riede et al. | |
| 4,310,416 A | 1/1982 | Tanaka et al. | |
| 4,317,725 A | 3/1982 | Kume et al. | |
| 4,342,651 A | 8/1982 | Ahrens | |
| 4,476,022 A | 10/1984 | Doll | |
| 4,486,303 A | 12/1984 | Brous | |
| 4,500,426 A | 2/1985 | Ishii et al. | |
| 4,508,622 A | 4/1985 | Polaschegg | |
| 4,536,201 A | 8/1985 | Brorsson et al. | |
| 4,624,784 A | 11/1986 | Lefebvre | |
| 4,647,748 A | 3/1987 | Glassman | |
| 4,661,246 A | 4/1987 | Ash | |
| 4,689,108 A | 8/1987 | Barry, Jr. et al. | |
| 4,756,835 A | 7/1988 | Wilson | |
| 4,769,134 A | 9/1988 | Allan et al. | |
| 4,770,787 A | 9/1988 | Heath et al. | |
| 4,773,991 A | 9/1988 | Aid | |
| 4,786,411 A | 11/1988 | Benattar et al. | |
| 4,827,430 A | 5/1989 | Aid et al. | |
| 4,869,421 A | 9/1989 | Norris et al. | |
| 4,875,619 A | 10/1989 | Anderson et al. | |
| 4,889,635 A | 12/1989 | Chevallet | |
| 4,894,164 A | 1/1990 | Polaschegg | |
| 4,923,613 A | 5/1990 | Chevallet | |
| 5,087,930 A | 2/1992 | Roy et al. | |
| 5,092,836 A | 3/1992 | Polaschegg | |
| 5,094,749 A | 3/1992 | Seita et al. | |
| 5,147,605 A | 9/1992 | Tatsuno et al. | |
| 5,227,049 A * | 7/1993 | Chevallet | A61M 1/30 210/104 |
| 5,232,145 A | 8/1993 | Alley et al. | |
| 5,236,476 A | 8/1993 | Klick | |
| 5,247,434 A | 9/1993 | Peterson et al. | |
| 5,259,961 A | 11/1993 | Eigendorf | |
| 5,312,550 A | 5/1994 | Hester | |
| 5,313,023 A | 5/1994 | Johnson | |
| 5,316,676 A | 5/1994 | Drori | |
| 5,326,476 A | 7/1994 | Grogan et al. | |
| 5,342,326 A | 8/1994 | Peppel et al. | |
| 5,344,392 A | 9/1994 | Senninger et al. | |
| 5,346,472 A | 9/1994 | Keshaviah et al. | |
| 5,360,395 A | 11/1994 | Utterberg | |
| 5,385,623 A | 1/1995 | Diaz | |
| 5,394,732 A | 3/1995 | Johnson et al. | |
| 5,395,351 A | 3/1995 | Munsch | |
| 5,401,238 A | 3/1995 | Pirazzoli | |
| 5,409,612 A | 4/1995 | Maltais et al. | |
| 5,421,208 A | 6/1995 | Packard et al. | |
| 5,439,451 A | 8/1995 | Collinson et al. | |
| 5,469,264 A | 11/1995 | Shigemori | |
| 5,472,614 A | 12/1995 | Rossi | |
| 5,489,385 A | 2/1996 | Raabe et al. | |
| 5,498,253 A | 3/1996 | Aswad et al. | |
| 5,498,338 A | 3/1996 | Kruger et al. | |
| 5,503,624 A | 4/1996 | Roeher et al. | |
| 5,520,640 A | 5/1996 | Utterberg | |
| 5,526,357 A | 6/1996 | Jandrell | |
| 5,533,996 A | 7/1996 | Murphey et al. | |
| 5,534,328 A | 7/1996 | Ashmead et al. | |
| 5,536,258 A | 7/1996 | Folden | |
| 5,580,460 A | 12/1996 | Polaschegg | |
| 5,580,523 A | 12/1996 | Bard | |
| 5,582,600 A | 12/1996 | Loh | |
| 5,591,016 A | 1/1997 | Kubota et al. | |
| 5,591,344 A | 1/1997 | Kenley et al. | |
| 5,593,581 A | 1/1997 | Lescoche | |
| 5,595,712 A | 1/1997 | Harbster et al. | |
| 5,609,770 A | 3/1997 | Zimmerman et al. | |
| 5,610,645 A | 3/1997 | Moore et al. | |
| 5,611,214 A | 3/1997 | Wegeng et al. | |
| 5,613,663 A | 3/1997 | Schmidt et al. | |
| 5,615,996 A | 4/1997 | Suzuki et al. | |
| 5,618,268 A | 4/1997 | Raines et al. | |
| 5,618,441 A | 4/1997 | Rosa et al. | |
| 5,620,608 A | 4/1997 | Rosa et al. | |
| 5,623,969 A | 4/1997 | Raines | |
| 5,624,572 A | 4/1997 | Larson et al. | |
| 5,629,871 A | 5/1997 | Love et al. | |
| 5,630,804 A | 5/1997 | Imada et al. | |
| 5,643,190 A | 7/1997 | Utterberg | |
| 5,647,984 A | 7/1997 | Hovland et al. | |
| 5,648,684 A | 7/1997 | Bertin et al. | |
| 5,650,071 A | 7/1997 | Brugger et al. | |
| 5,662,144 A | 9/1997 | Lo et al. | |
| 5,685,835 A | 11/1997 | Brugger | |
| 5,689,966 A | 11/1997 | Zess et al. | |
| 5,693,008 A | 12/1997 | Brugger et al. | |
| 5,698,916 A | 12/1997 | Eguchi | |
| 5,711,883 A | 1/1998 | Folden et al. | |
| 5,713,850 A | 2/1998 | Heilmann et al. | |
| 5,725,773 A | 3/1998 | Polaschegg | |
| 5,743,892 A | 4/1998 | Loh et al. | |
| 5,744,031 A | 4/1998 | Bene | |
| 5,749,226 A | 5/1998 | Bowman et al. | |
| 5,769,985 A | 6/1998 | Kawakami et al. | |
| 5,779,833 A | 7/1998 | Cawley et al. | |
| 5,782,575 A | 7/1998 | Vincent et al. | |
| 5,788,099 A | 8/1998 | Treu et al. | |
| 5,788,851 A | 8/1998 | Kenley et al. | |
| 5,792,367 A | 8/1998 | Mattisson et al. | |
| 5,811,062 A | 9/1998 | Wegeng et al. | |
| 5,813,235 A | 9/1998 | Peterson | |
| 5,851,202 A | 12/1998 | Carlsson | |
| 5,858,238 A | 1/1999 | Mcrea et al. | |
| 5,858,239 A | 1/1999 | Kenley et al. | |
| 5,861,555 A | 1/1999 | Hobro et al. | |
| 5,868,930 A | 2/1999 | Kopf | |

(56) References Cited

U.S. PATENT DOCUMENTS

| | | |
|---|---|---|
| 5,879,316 A | 3/1999 | Safar et al. |
| 5,881,774 A | 3/1999 | Utterberg |
| 5,885,456 A | 3/1999 | Charkoudian et al. |
| 5,895,368 A | 4/1999 | Utterberg |
| 5,903,211 A | 5/1999 | Flego et al. |
| 5,910,138 A | 6/1999 | Sperko et al. |
| 5,914,033 A | 6/1999 | Carlsson |
| 5,921,678 A | 7/1999 | Desai et al. |
| 5,928,177 A | 7/1999 | Brugger et al. |
| 5,928,180 A | 7/1999 | Krivitski et al. |
| 5,932,103 A | 8/1999 | Kenley et al. |
| 5,932,940 A | 8/1999 | Epstein et al. |
| 5,938,634 A | 8/1999 | Packard |
| 5,938,938 A | 8/1999 | Bosetto et al. |
| 5,951,863 A | 9/1999 | Kruger et al. |
| 5,951,870 A | 9/1999 | Utterberg |
| 5,957,898 A | 9/1999 | Jepson et al. |
| 5,974,867 A | 11/1999 | Forster et al. |
| 5,976,115 A | 11/1999 | Parris et al. |
| 5,983,947 A | 11/1999 | Utterberg |
| 5,984,903 A | 11/1999 | Nadal |
| 5,993,174 A | 11/1999 | Konishi |
| 6,003,556 A | 12/1999 | Brugger et al. |
| 6,010,623 A | 1/2000 | Schnell et al. |
| 6,024,276 A | 2/2000 | Hirata et al. |
| 6,032,926 A | 3/2000 | Fuchs |
| 6,036,680 A | 3/2000 | Horne et al. |
| 6,039,877 A | 3/2000 | Chevallet et al. |
| 6,041,801 A | 3/2000 | Gray et al. |
| 6,044,691 A | 4/2000 | Kenley et al. |
| 6,048,432 A | 4/2000 | Ecer |
| 6,058,934 A | 5/2000 | Sullivan |
| 6,064,797 A | 5/2000 | Crittendon et al. |
| 6,066,261 A | 5/2000 | Spickermann |
| 6,071,269 A | 6/2000 | Schnell et al. |
| 6,074,559 A | 6/2000 | Hahmann et al. |
| 6,077,443 A | 6/2000 | Goldau |
| 6,082,891 A | 7/2000 | Schubert et al. |
| 6,100,463 A | 8/2000 | Ladd et al. |
| 6,109,994 A | 8/2000 | Cho et al. |
| 6,113,785 A | 9/2000 | Miura et al. |
| 6,117,115 A | 9/2000 | Hill et al. |
| 6,117,123 A | 9/2000 | Barney et al. |
| 6,121,539 A | 9/2000 | Johnson et al. |
| 6,123,798 A | 9/2000 | Gandhi et al. |
| 6,126,723 A | 10/2000 | Drost et al. |
| 6,126,831 A | 10/2000 | Goldau et al. |
| 6,129,973 A | 10/2000 | Martin et al. |
| 6,132,616 A | 10/2000 | Twardowski et al. |
| 6,139,754 A | 10/2000 | Hartranft et al. |
| 6,142,008 A | 11/2000 | Cole et al. |
| 6,143,181 A | 11/2000 | Falkvall et al. |
| 6,143,247 A | 11/2000 | Sheppard et al. |
| 6,148,635 A | 11/2000 | Beebe et al. |
| 6,153,102 A | 11/2000 | Kenley et al. |
| 6,165,149 A | 12/2000 | Utterberg et al. |
| 6,165,161 A | 12/2000 | York et al. |
| 6,167,910 B1 | 1/2001 | Chow |
| 6,187,198 B1 | 2/2001 | Utterberg |
| 6,187,199 B1 | 2/2001 | Goldau |
| 6,192,596 B1 | 2/2001 | Bennett et al. |
| 6,193,462 B1 | 2/2001 | Kubota |
| 6,202,312 B1 | 3/2001 | Rando |
| 6,203,522 B1 | 3/2001 | Holmberg et al. |
| 6,203,535 B1 | 3/2001 | Barney et al. |
| 6,212,333 B1 | 4/2001 | Oik et al. |
| 6,220,299 B1 | 4/2001 | Arvidsson et al. |
| 6,221,040 B1 | 4/2001 | Kleinekofort |
| 6,221,064 B1 | 4/2001 | Nadal |
| 6,223,130 B1 | 4/2001 | Gray et al. |
| 6,225,497 B1 | 5/2001 | Becker et al. |
| 6,234,773 B1 | 5/2001 | Hill et al. |
| 6,251,279 B1 | 6/2001 | Peterson et al. |
| 6,254,567 B1 | 7/2001 | Treu et al. |
| 6,254,754 B1 | 7/2001 | Ross et al. |
| 6,258,276 B1 | 7/2001 | Mika et al. |
| 6,261,282 B1 | 7/2001 | Jepson et al. |
| 6,277,277 B1 | 8/2001 | Jacobi et al. |
| 6,280,406 B1 | 8/2001 | Dolecek et al. |
| 6,284,141 B1 | 9/2001 | Shaldon et al. |
| 6,302,653 B1 | 10/2001 | Bryant et al. |
| 6,308,721 B1 | 10/2001 | Bock et al. |
| 6,309,673 B1 | 10/2001 | Duponchelle et al. |
| 6,322,551 B1 | 11/2001 | Brugger |
| 6,323,662 B2 | 11/2001 | Ferri |
| 6,325,774 B1 | 12/2001 | Bene et al. |
| 6,329,139 B1 | 12/2001 | Nova et al. |
| 6,331,252 B1 | 12/2001 | El Sayyid et al. |
| 6,334,301 B1 | 1/2002 | Otsap et al. |
| 6,343,614 B1 | 2/2002 | Gray et al. |
| 6,344,033 B1 | 2/2002 | Jepson et al. |
| 6,346,084 B1 | 2/2002 | Schnell et al. |
| 6,347,711 B1 | 2/2002 | Goebel et al. |
| 6,349,170 B1 | 2/2002 | Fressinet et al. |
| 6,350,260 B1 | 2/2002 | Goebel et al. |
| 6,355,161 B1 | 3/2002 | Shah et al. |
| 6,357,332 B1 | 3/2002 | Vecchio |
| 6,365,041 B1 | 4/2002 | Hoadley |
| 6,368,505 B1 | 4/2002 | Grummert et al. |
| 6,375,871 B1 | 4/2002 | Bentsen et al. |
| 6,382,923 B1 | 5/2002 | Gray |
| 6,387,069 B1 | 5/2002 | Utterberg |
| 6,395,180 B2 | 5/2002 | Chioini et al. |
| 6,415,860 B1 | 7/2002 | Kelly et al. |
| 6,416,293 B1 | 7/2002 | Bouchard et al. |
| 6,423,022 B1 | 7/2002 | Roeher et al. |
| 6,432,309 B1 | 8/2002 | Fuke et al. |
| 6,454,736 B1 | 9/2002 | Ludt et al. |
| 6,454,942 B1 | 9/2002 | Shintani et al. |
| 6,468,056 B1 | 10/2002 | Murakoshi |
| 6,477,058 B1 | 11/2002 | Luebs et al. |
| 6,481,982 B1 | 11/2002 | Yokomichi |
| 6,485,263 B1 | 11/2002 | Bryant et al. |
| 6,488,842 B2 | 12/2002 | Nagaoka |
| 6,488,872 B1 | 12/2002 | Beebe et al. |
| 6,503,062 B1 | 1/2003 | Gray et al. |
| 6,514,225 B1 | 2/2003 | Utterberg et al. |
| 6,514,412 B1 | 2/2003 | Insley |
| 6,526,357 B1 | 2/2003 | Soussan et al. |
| 6,527,728 B2 | 3/2003 | Zhang |
| 6,530,262 B1 | 3/2003 | Esser |
| 6,536,742 B2 | 3/2003 | Lotz et al. |
| 6,537,506 B1 | 3/2003 | Schwalbe et al. |
| 6,544,229 B1 | 4/2003 | Danby et al. |
| 6,546,998 B2 | 4/2003 | Oh et al. |
| 6,554,789 B1 | 4/2003 | Brugger et al. |
| 6,572,576 B2 | 6/2003 | Brugger et al. |
| 6,572,641 B2 | 6/2003 | Brugger et al. |
| 6,575,927 B1 | 6/2003 | Weitzel et al. |
| 6,579,241 B2 | 6/2003 | Roeher |
| 6,579,253 B1 | 6/2003 | Burbank et al. |
| 6,581,906 B2 | 6/2003 | Pott et al. |
| 6,582,385 B2 | 6/2003 | Burbank et al. |
| 6,592,558 B2 | 7/2003 | Quah |
| 6,601,432 B1 | 8/2003 | Ericson et al. |
| 6,602,424 B1 | 8/2003 | Krämer et al. |
| 6,604,908 B1 | 8/2003 | Bryant et al. |
| 6,607,644 B1 | 8/2003 | Apffel, Jr. |
| 6,607,697 B1 | 8/2003 | Muller |
| 6,616,877 B2 | 9/2003 | Close et al. |
| 6,616,909 B1 | 9/2003 | Tonkovich et al. |
| 6,623,860 B2 | 9/2003 | Hu et al. |
| 6,630,068 B1 | 10/2003 | Vinci |
| 6,635,226 B1 | 10/2003 | Tso et al. |
| 6,640,611 B2 | 11/2003 | Ericson et al. |
| 6,649,046 B2 | 11/2003 | Chevallet |
| 6,649,063 B2 | 11/2003 | Brugger et al. |
| 6,652,627 B1 | 11/2003 | Tonkovich et al. |
| 6,653,841 B1 | 11/2003 | Koerdt et al. |
| 6,654,660 B1 | 11/2003 | Singh et al. |
| 6,666,840 B1 | 12/2003 | Falkvall et al. |
| 6,666,909 B1 | 12/2003 | Tegrotenhuis et al. |
| 6,672,502 B1 | 1/2004 | Paul et al. |
| 6,673,311 B1 | 1/2004 | Sotoyama et al. |

(56) References Cited

U.S. PATENT DOCUMENTS

| | | |
|---|---|---|
| 6,676,621 B1 | 1/2004 | Menninger |
| 6,676,835 B2 | 1/2004 | O'Connor et al. |
| 6,684,710 B2 | 2/2004 | Chevallet et al. |
| 6,685,831 B2 | 2/2004 | Dönig et al. |
| 6,686,946 B2 | 2/2004 | Masuda et al. |
| 6,688,381 B2 | 2/2004 | Pence et al. |
| 6,695,807 B2 | 2/2004 | Bell et al. |
| 6,716,356 B2 | 4/2004 | Collins et al. |
| 6,730,233 B2 | 5/2004 | Pedrazzi |
| 6,731,216 B2 | 5/2004 | Ho et al. |
| 6,733,676 B2 | 5/2004 | Takai |
| 6,736,789 B1 | 5/2004 | Spickermann |
| 6,738,052 B1 | 5/2004 | Manke et al. |
| 6,743,193 B2 | 6/2004 | Brugger et al. |
| 6,744,038 B2 | 6/2004 | Wang et al. |
| 6,746,514 B2 | 6/2004 | Bedingfield et al. |
| 6,749,814 B1 | 6/2004 | Bergh et al. |
| 6,767,333 B1 | 7/2004 | Mller et al. |
| 6,775,577 B2 | 8/2004 | Crnkovich et al. |
| 6,793,831 B1 | 9/2004 | Paul et al. |
| 6,797,056 B2 | 9/2004 | David |
| 6,804,991 B2 | 10/2004 | Balschat et al. |
| 6,806,947 B1 | 10/2004 | Ekdahl et al. |
| 6,811,707 B2 | 11/2004 | Rovatti et al. |
| 6,814,547 B2 | 11/2004 | Childers et al. |
| 6,814,726 B1 | 11/2004 | Lauer |
| 6,814,859 B2 | 11/2004 | Koehler et al. |
| 6,818,179 B1 | 11/2004 | Edgson et al. |
| 6,821,432 B2 | 11/2004 | Metzner |
| 6,827,698 B1 | 12/2004 | Kleinekofort |
| 6,830,693 B2 | 12/2004 | Govoni et al. |
| 6,838,156 B1 | 1/2005 | Neyer et al. |
| 6,852,231 B2 | 2/2005 | Ivansons et al. |
| 6,858,137 B2 | 2/2005 | Hahmann et al. |
| 6,863,867 B2 | 3/2005 | Vanden Bussche et al. |
| 6,868,309 B1 | 3/2005 | Begelman |
| 6,869,538 B2 | 3/2005 | Yu et al. |
| 6,871,838 B2 | 3/2005 | Raines et al. |
| 6,877,713 B1 | 4/2005 | Gray et al. |
| 6,878,283 B2 | 4/2005 | Thompson |
| 6,880,034 B2 | 4/2005 | Manke et al. |
| 6,881,344 B2 | 4/2005 | Vasta et al. |
| 6,889,556 B2 | 5/2005 | Steger |
| 6,892,781 B2 | 5/2005 | Mcherron et al. |
| 6,903,332 B2 | 6/2005 | Weiss et al. |
| 6,905,479 B1 | 6/2005 | Bouchard et al. |
| 6,911,262 B2 | 6/2005 | Sallavanti et al. |
| 6,913,877 B1 | 7/2005 | Chaplen et al. |
| 6,929,751 B2 | 8/2005 | Bowman, Jr. et al. |
| 6,936,031 B2 | 8/2005 | Caleffi |
| 6,939,111 B2 | 9/2005 | Huitt et al. |
| 6,939,471 B2 | 9/2005 | Gross et al. |
| 6,952,963 B2 | 10/2005 | Delnevo |
| 6,953,323 B2 | 10/2005 | Childers et al. |
| 6,955,655 B2 | 10/2005 | Burbank et al. |
| 6,967,002 B1 | 11/2005 | Edgson et al. |
| 6,974,301 B2 | 12/2005 | Suzuki et al. |
| 6,976,964 B2 | 12/2005 | Chevallet et al. |
| 6,979,309 B2 | 12/2005 | Burbank et al. |
| 6,981,522 B2 | 1/2006 | O'Connor et al. |
| 6,986,428 B2 | 1/2006 | Hester et al. |
| 6,989,134 B2 | 1/2006 | Tonkovich et al. |
| 6,994,829 B2 | 2/2006 | Whyatt et al. |
| 7,004,924 B1 | 2/2006 | Brugger et al. |
| 7,014,705 B2 | 3/2006 | David |
| 7,021,148 B2 | 4/2006 | Kuhn et al. |
| 7,022,098 B2 | 4/2006 | Wariar et al. |
| 7,029,456 B2 | 4/2006 | Ware et al. |
| 7,033,498 B2 | 4/2006 | Wong |
| 7,033,539 B2 | 4/2006 | Krensky et al. |
| 7,040,142 B2 | 5/2006 | Burbank |
| 7,044,432 B2 | 5/2006 | Beden et al. |
| 7,044,927 B2 | 5/2006 | Mueller et al. |
| 7,063,512 B2 | 6/2006 | Haesloop et al. |
| 7,070,589 B2 | 7/2006 | Lolachi et al. |
| 7,074,191 B2 | 7/2006 | Bosetto et al. |
| 7,087,033 B2 | 8/2006 | Brugger et al. |
| 7,087,036 B2 | 8/2006 | Busby et al. |
| 7,094,345 B2 | 8/2006 | Gilbert et al. |
| 7,112,273 B2 | 9/2006 | Weigel et al. |
| 7,114,701 B2 | 10/2006 | Peppel |
| 7,115,206 B2 | 10/2006 | Chevallet et al. |
| 7,115,228 B2 | 10/2006 | Lundtveit et al. |
| 7,118,920 B2 | 10/2006 | Brophy et al. |
| 7,121,815 B2 | 10/2006 | Knuth et al. |
| 7,122,149 B2 | 10/2006 | Li et al. |
| 7,122,156 B2 | 10/2006 | Bergh et al. |
| 7,125,540 B1 | 10/2006 | Wegeng et al. |
| 7,131,956 B1 | 11/2006 | Pirazzoli et al. |
| 7,147,615 B2 | 12/2006 | Wariar et al. |
| 7,150,815 B2 | 12/2006 | Ashmead et al. |
| 7,152,469 B2 | 12/2006 | Milleker et al. |
| 7,163,531 B2 | 1/2007 | Seese et al. |
| 7,166,084 B2 | 1/2007 | Utterberg |
| 7,168,334 B1 | 1/2007 | Drott |
| 7,170,591 B2 | 1/2007 | Ohishi et al. |
| 7,175,697 B2 | 2/2007 | Neri |
| 7,186,342 B2 | 3/2007 | Pirazzoli et al. |
| 7,188,151 B2 | 3/2007 | Kumar et al. |
| 7,211,442 B2 | 5/2007 | Gilbert et al. |
| 7,214,312 B2 | 5/2007 | Brugger et al. |
| 7,217,108 B2 | 5/2007 | Herwig et al. |
| 7,217,364 B2 | 5/2007 | Lauer et al. |
| 7,223,262 B2 | 5/2007 | Brehm et al. |
| 7,223,338 B2 | 5/2007 | Duchamp et al. |
| 7,232,418 B2 | 6/2007 | Neri et al. |
| 7,238,164 B2 | 7/2007 | Childers et al. |
| 7,247,146 B2 | 7/2007 | Tonelli et al. |
| 7,279,134 B2 | 10/2007 | Chan et al. |
| 7,291,123 B2 | 11/2007 | Baraldi et al. |
| 7,306,197 B2 | 12/2007 | Parrino et al. |
| 7,314,061 B2 | 1/2008 | Peppel |
| 7,316,780 B1 | 1/2008 | Fendya et al. |
| 7,337,674 B2 | 3/2008 | Burbank et al. |
| 7,341,568 B2 | 3/2008 | Zhang |
| 7,354,426 B2 | 4/2008 | Young |
| 7,355,685 B2 | 4/2008 | Scibona et al. |
| 7,378,280 B2 | 5/2008 | Quake et al. |
| 7,381,195 B2 | 6/2008 | Mori et al. |
| 7,393,337 B2 | 7/2008 | Tonelli et al. |
| 7,402,249 B2 | 7/2008 | Ikeda |
| 7,469,716 B2 | 12/2008 | Parrino et al. |
| 7,470,265 B2 | 12/2008 | Brugger et al. |
| 7,488,301 B2 | 2/2009 | Beden et al. |
| 7,488,447 B2 | 2/2009 | Sternby |
| 7,493,824 B2 | 2/2009 | Brucksch et al. |
| 7,494,590 B2 | 2/2009 | Felding et al. |
| 7,503,908 B2 | 3/2009 | Bartholomew |
| 7,507,380 B2 | 3/2009 | Chang et al. |
| 7,510,545 B2 | 3/2009 | Peppel |
| 7,517,332 B2 | 4/2009 | Tonelli et al. |
| 7,517,387 B2 | 4/2009 | Chevallet et al. |
| 7,520,919 B2 | 4/2009 | Caleffi |
| 7,537,687 B2 | 5/2009 | Toyoda et al. |
| 7,544,300 B2 | 6/2009 | Brugger et al. |
| 7,551,043 B2 | 6/2009 | Nguyen et al. |
| 7,559,911 B2 | 7/2009 | Giannella |
| 7,575,562 B2 | 8/2009 | Oishi et al. |
| 7,575,564 B2 | 8/2009 | Childers |
| 7,591,449 B2 | 9/2009 | Raines et al. |
| 7,603,907 B2 | 10/2009 | Reiter et al. |
| 7,615,035 B2 | 11/2009 | Peppel |
| 7,618,531 B2 | 11/2009 | Sugioka et al. |
| 7,622,043 B2 | 11/2009 | Sawada et al. |
| 7,632,470 B2 | 12/2009 | Tabata et al. |
| 7,647,834 B2 | 1/2010 | O'Mahony et al. |
| 7,648,474 B2 | 1/2010 | Paolini et al. |
| 7,648,476 B2 | 1/2010 | Bock et al. |
| 7,648,792 B2 | 1/2010 | Kaschmitter et al. |
| 7,656,527 B2 | 2/2010 | Scarpaci |
| 7,661,294 B2 | 2/2010 | Dam |
| 7,671,974 B2 | 3/2010 | O'Mahony et al. |
| 7,682,328 B2 | 3/2010 | Han et al. |
| 7,686,778 B2 | 3/2010 | Burbank et al. |

(56) References Cited

U.S. PATENT DOCUMENTS

| | | |
|---|---|---|
| 7,699,992 B2 | 4/2010 | Sternby |
| 7,708,714 B2 | 5/2010 | Connell et al. |
| 7,713,226 B2 | 5/2010 | Ash et al. |
| 7,726,361 B2 | 6/2010 | Bartholomew |
| 7,727,220 B2 | 6/2010 | Wieslander et al. |
| 7,744,553 B2 | 6/2010 | Kelly et al. |
| 7,749,184 B2 | 7/2010 | Cavalcanti et al. |
| 7,758,082 B2 | 7/2010 | Weigel et al. |
| 7,758,547 B2 | 7/2010 | Tonelli et al. |
| 7,771,379 B2 | 8/2010 | Treu |
| 7,771,380 B2 | 8/2010 | Jönsson et al. |
| 7,775,986 B2 | 8/2010 | Roeher et al. |
| 7,776,219 B2 | 8/2010 | Brugger et al. |
| 7,780,848 B2 | 8/2010 | Kim et al. |
| 7,788,038 B2 | 8/2010 | Oshita et al. |
| 7,790,029 B2 | 9/2010 | Dannenmaier et al. |
| 7,794,141 B2 | 9/2010 | Perry et al. |
| 7,794,419 B2 | 9/2010 | Paolini et al. |
| 7,801,746 B2 | 9/2010 | Moll et al. |
| 7,815,852 B2 | 10/2010 | Sternby |
| 7,824,354 B2 | 11/2010 | Vinci et al. |
| 7,873,489 B2 | 1/2011 | Dolgos et al. |
| 7,896,831 B2 | 3/2011 | Sternby et al. |
| 7,901,579 B2 | 3/2011 | Brugger et al. |
| 7,913,751 B2 | 3/2011 | Zwittig |
| 7,918,993 B2 | 4/2011 | Harraway |
| 7,922,899 B2 | 4/2011 | Vasta et al. |
| 7,955,504 B1 | 6/2011 | Jovanovic et al. |
| 7,968,250 B2 | 6/2011 | Kaschmitter et al. |
| 8,002,727 B2 | 8/2011 | Brugger et al. |
| 8,012,114 B2 | 9/2011 | Daniel et al. |
| 8,075,509 B2 | 12/2011 | Molducci et al. |
| 8,105,265 B2 | 1/2012 | Demers et al. |
| 8,128,822 B2 | 3/2012 | Browning et al. |
| 8,137,554 B2 | 3/2012 | Jovanovic et al. |
| 8,182,440 B2 | 5/2012 | Cruz et al. |
| 8,182,691 B2 | 5/2012 | Stahl |
| 8,190,651 B2 | 5/2012 | Treu et al. |
| 8,192,387 B2 | 6/2012 | Brugger et al. |
| 8,210,049 B2 | 7/2012 | Brugger |
| 8,235,931 B2 | 8/2012 | Burbank et al. |
| 8,236,599 B2 | 8/2012 | Chang et al. |
| 8,267,881 B2 | 9/2012 | O'Mahony et al. |
| 8,273,245 B2 | 9/2012 | Jovanovic et al. |
| 8,293,113 B2 | 10/2012 | Jönsson et al. |
| 8,293,114 B2 | 10/2012 | Jönsson et al. |
| 8,298,427 B2 | 10/2012 | Ficheux et al. |
| 8,323,492 B2 | 12/2012 | Childers et al. |
| 8,329,030 B2 | 12/2012 | Childers et al. |
| 8,343,085 B2 | 1/2013 | Toyoda et al. |
| 8,394,046 B2 | 3/2013 | Nuernberger et al. |
| 8,414,182 B2 | 4/2013 | Paul et al. |
| 8,419,945 B2 | 4/2013 | Browning et al. |
| 8,449,487 B2 | 5/2013 | Hovland et al. |
| 8,460,228 B2 | 6/2013 | Burbank et al. |
| 8,475,398 B2 | 7/2013 | O'Mahony |
| 8,491,518 B2 | 7/2013 | Schnell et al. |
| 8,496,824 B2 | 7/2013 | Remkes et al. |
| 8,501,009 B2 | 8/2013 | Peterson et al. |
| 8,506,536 B2 | 8/2013 | Schnell |
| 8,512,553 B2 | 8/2013 | Cicchello et al. |
| 8,512,554 B2 | 8/2013 | Yu et al. |
| 8,524,086 B2 | 9/2013 | Peterson et al. |
| 8,529,491 B2 | 9/2013 | Beiriger |
| 8,535,525 B2 | 9/2013 | Heyes et al. |
| 8,603,020 B2 | 12/2013 | Roger et al. |
| 8,608,658 B2 | 12/2013 | Burbank et al. |
| 8,647,290 B2 | 2/2014 | Masala et al. |
| 8,679,348 B2 | 3/2014 | Burbank et al. |
| 8,685,244 B2 | 4/2014 | Heyes et al. |
| 8,685,251 B2 | 4/2014 | Smejtek et al. |
| 8,753,515 B2 | 6/2014 | Curtis et al. |
| 8,801,922 B2 | 8/2014 | Wrazel et al. |
| 8,840,581 B2 | 9/2014 | McGill et al. |
| 9,024,746 B2 | 5/2015 | Burbank et al. |
| 9,097,370 B2 | 8/2015 | Schnell et al. |
| 9,138,687 B2 | 9/2015 | Peterson et al. |
| 9,220,825 B2 | 12/2015 | Buckberry |
| 9,220,828 B2 | 12/2015 | Coates |
| 9,283,320 B2 | 3/2016 | Brugger et al. |
| 9,480,455 B2 | 11/2016 | Buckberry |
| 9,482,218 B2 | 11/2016 | Coates et al. |
| 9,592,029 B2 | 3/2017 | Buckberry |
| 9,636,444 B2 | 5/2017 | Burbank et al. |
| 9,700,663 B2 | 7/2017 | Burbank et al. |
| 9,835,509 B2 | 12/2017 | Brugger et al. |
| 9,879,807 B2 | 1/2018 | Brugger et al. |
| 2002/0023879 A1 | 2/2002 | Hadden |
| 2002/0032398 A1 | 3/2002 | Steele et al. |
| 2002/0108859 A1 | 8/2002 | Wang et al. |
| 2002/0108869 A1 | 8/2002 | Savtchenko |
| 2002/0115200 A1 | 8/2002 | Zou et al. |
| 2002/0162784 A1 | 11/2002 | Kohlheb et al. |
| 2002/0187069 A1 | 12/2002 | Levin et al. |
| 2003/0010717 A1 | 1/2003 | Brugger et al. |
| 2003/0039169 A1 | 2/2003 | Ehrfeld et al. |
| 2003/0052429 A1 | 3/2003 | Vigna et al. |
| 2003/0082066 A1 | 5/2003 | Hajaligol et al. |
| 2003/0138349 A1 | 7/2003 | Robinson et al. |
| 2003/0156991 A1 | 8/2003 | Halas et al. |
| 2003/0163077 A1 | 8/2003 | Kim et al. |
| 2003/0183345 A1 | 10/2003 | Soberay |
| 2003/0220598 A1 | 11/2003 | Busby et al. |
| 2004/0004589 A1 | 1/2004 | Shih |
| 2004/0008370 A1 | 1/2004 | Keane et al. |
| 2004/0012122 A1 | 1/2004 | Nagaoka et al. |
| 2004/0016700 A1 | 1/2004 | Kellam et al. |
| 2004/0020286 A1 | 2/2004 | Blakley et al. |
| 2004/0022691 A1 | 2/2004 | Allen et al. |
| 2004/0035452 A1 | 2/2004 | Ma |
| 2004/0035462 A1 | 2/2004 | McCarty et al. |
| 2004/0072278 A1 | 4/2004 | Chou et al. |
| 2004/0084370 A1 | 5/2004 | Singh et al. |
| 2004/0084371 A1 | 5/2004 | Kellam et al. |
| 2004/0086427 A1 | 5/2004 | Childers et al. |
| 2004/0125689 A1 | 7/2004 | Ehrfeld et al. |
| 2004/0157096 A1 | 8/2004 | Peterson |
| 2004/0158189 A1 | 8/2004 | Tonelli et al. |
| 2004/0208751 A1 | 10/2004 | Lazar et al. |
| 2004/0215129 A1 | 10/2004 | Edgson et al. |
| 2004/0256230 A1 | 12/2004 | Yager et al. |
| 2005/0006296 A1 | 1/2005 | Sullivan et al. |
| 2005/0007748 A1 | 1/2005 | Callahan et al. |
| 2005/0040110 A1* | 2/2005 | Felding ............... A61M 1/1656 210/646 |
| 2005/0070837 A1 | 3/2005 | Ferrarini et al. |
| 2005/0074834 A1 | 4/2005 | Chaplen et al. |
| 2005/0082225 A1 | 4/2005 | Kreymann |
| 2005/0126211 A1 | 6/2005 | Drost et al. |
| 2005/0129580 A1 | 6/2005 | Swinehart et al. |
| 2005/0131332 A1 | 6/2005 | Kelly et al. |
| 2005/0145497 A1 | 7/2005 | Gilbert et al. |
| 2005/0179748 A1 | 8/2005 | Malik et al. |
| 2005/0202557 A1 | 9/2005 | Borenstein et al. |
| 2006/0046113 A1 | 3/2006 | Wang et al. |
| 2006/0079698 A1 | 4/2006 | Joshi et al. |
| 2006/0157413 A1 | 7/2006 | Bene et al. |
| 2006/0174715 A1 | 8/2006 | Wehrs et al. |
| 2006/0200064 A1 | 9/2006 | Gross et al. |
| 2006/0266692 A1 | 11/2006 | Foster et al. |
| 2007/0020400 A1 | 1/2007 | Chang |
| 2007/0029365 A1 | 2/2007 | Paul et al. |
| 2007/0119771 A1 | 5/2007 | Schukar et al. |
| 2007/0125489 A1 | 6/2007 | Paul et al. |
| 2007/0128707 A1 | 6/2007 | Rorrer et al. |
| 2007/0131403 A1 | 6/2007 | Vetrovec et al. |
| 2007/0158249 A1 | 7/2007 | Ash |
| 2007/0158268 A1 | 7/2007 | Decomo |
| 2007/0184576 A1 | 8/2007 | Chang et al. |
| 2007/0215644 A1 | 9/2007 | Otis et al. |
| 2007/0278155 A1 | 12/2007 | Lo et al. |
| 2007/0295651 A1 | 12/2007 | Martinez et al. |
| 2008/0006040 A1 | 1/2008 | Peterson et al. |
| 2008/0009780 A1 | 1/2008 | Leonard et al. |

(56) References Cited

U.S. PATENT DOCUMENTS

| | | |
|---|---|---|
| 2008/0053842 A1 | 3/2008 | Williams et al. |
| 2008/0097274 A1 | 4/2008 | Neri et al. |
| 2008/0108122 A1 | 5/2008 | Paul et al. |
| 2008/0108930 A1 | 5/2008 | Weitzel et al. |
| 2008/0149563 A1 | 6/2008 | Ash |
| 2008/0196725 A1 | 8/2008 | Mele |
| 2008/0200858 A1 | 8/2008 | Ichiishi et al. |
| 2008/0296226 A1 | 12/2008 | Gotch |
| 2009/0008331 A1 | 1/2009 | Wilt et al. |
| 2009/0012452 A1 | 1/2009 | Slepicka et al. |
| 2009/0038393 A1* | 2/2009 | Chaung ............... G01F 23/2921 73/290 R |
| 2009/0076433 A1* | 3/2009 | Folden ................ A61M 1/3643 604/4.01 |
| 2009/0087326 A1 | 4/2009 | Voltenburg et al. |
| 2009/0092526 A1 | 4/2009 | Miller |
| 2009/0095679 A1 | 4/2009 | Demers et al. |
| 2009/0101549 A1 | 4/2009 | Kamen et al. |
| 2009/0101576 A1 | 4/2009 | Rohde et al. |
| 2009/0114595 A1 | 5/2009 | Wallenas et al. |
| 2009/0124963 A1 | 5/2009 | Hogard et al. |
| 2009/0165366 A1 | 7/2009 | Jovanovic et al. |
| 2009/0211977 A1 | 8/2009 | Miller |
| 2009/0230036 A1 | 9/2009 | Apel et al. |
| 2009/0306573 A1 | 12/2009 | Gagner et al. |
| 2009/0309835 A1 | 12/2009 | Levin et al. |
| 2009/0312686 A1 | 12/2009 | Sakamoto et al. |
| 2010/0018923 A1 | 1/2010 | Rohde et al. |
| 2010/0022934 A1 | 1/2010 | Hogard |
| 2010/0051552 A1 | 3/2010 | Rohde et al. |
| 2010/0078385 A1 | 4/2010 | Kawarabata et al. |
| 2010/0089807 A1* | 4/2010 | Heyes .................... A61M 1/16 210/96.2 |
| 2010/0192686 A1 | 8/2010 | Kamen et al. |
| 2010/0271296 A1 | 10/2010 | Kopychev et al. |
| 2010/0292627 A1 | 11/2010 | Caleffi et al. |
| 2010/0292657 A1 | 11/2010 | Fontanazzi et al. |
| 2010/0292944 A1 | 11/2010 | Howell et al. |
| 2010/0321046 A1 | 12/2010 | Randall et al. |
| 2010/0326914 A1 | 12/2010 | Drost et al. |
| 2011/0005986 A1 | 1/2011 | Kelly et al. |
| 2011/0105979 A1 | 5/2011 | Schlaeper et al. |
| 2011/0106466 A1 | 5/2011 | Furmanski et al. |
| 2011/0132841 A1 | 6/2011 | Rohde et al. |
| 2011/0186517 A1 | 8/2011 | Hedmann et al. |
| 2011/0189048 A1 | 8/2011 | Curtis et al. |
| 2011/0257579 A1 | 10/2011 | Rossi et al. |
| 2011/0295175 A1 | 12/2011 | Felder et al. |
| 2012/0029937 A1 | 2/2012 | Neftel et al. |
| 2012/0065581 A1 | 3/2012 | Childers et al. |
| 2012/0103902 A1 | 5/2012 | Childers et al. |
| 2012/0138533 A1 | 6/2012 | Curtis et al. |
| 2012/0226236 A1 | 9/2012 | Fini et al. |
| 2012/0267291 A1 | 10/2012 | Coates |
| 2012/0292246 A1 | 11/2012 | Jovanovic et al. |
| 2012/0298580 A1 | 11/2012 | Gronau et al. |
| 2012/0318740 A1 | 12/2012 | Ekdahl et al. |
| 2013/0018301 A1 | 1/2013 | Weaver et al. |
| 2013/0020237 A1 | 1/2013 | Wilt et al. |
| 2013/0030344 A1 | 1/2013 | Gronau et al. |
| 2013/0037485 A1 | 2/2013 | Wilt et al. |
| 2013/0056418 A1 | 3/2013 | Kopperschmidt et al. |
| 2013/0056419 A1 | 3/2013 | Curtis |
| 2013/0060233 A1 | 3/2013 | O'Connor et al. |
| 2013/0092361 A1 | 4/2013 | Wrazel et al. |
| 2013/0146541 A1 | 6/2013 | Weigel et al. |
| 2013/0180339 A1 | 7/2013 | Brugger |
| 2013/0186829 A1 | 7/2013 | Callan et al. |
| 2013/0206693 A2 | 8/2013 | Thys |
| 2013/0213890 A1 | 8/2013 | Kelly et al. |
| 2013/0267883 A1 | 10/2013 | Medrano |
| 2013/0303963 A1 | 11/2013 | Breuch et al. |
| 2014/0014580 A1 | 1/2014 | Ritter |
| 2014/0018727 A1 | 1/2014 | Burbank et al. |
| 2014/0021111 A1 | 1/2014 | Roger et al. |
| 2014/0069861 A1 | 3/2014 | Browning et al. |
| 2014/0072288 A1 | 3/2014 | Newell |
| 2014/0076058 A1 | 3/2014 | Brugger et al. |
| 2014/0158589 A1* | 6/2014 | Furuhashi ............... A61M 1/14 210/97 |
| 2014/0178215 A1 | 6/2014 | Baxter et al. |
| 2014/0209540 A1 | 7/2014 | Smejtek et al. |
| 2014/0276424 A1 | 9/2014 | Davis et al. |
| 2014/0291243 A1 | 10/2014 | Curtis et al. |
| 2014/0299545 A1 | 10/2014 | Wrazel et al. |
| 2014/0319035 A1 | 10/2014 | Burbank et al. |
| 2015/0005699 A1 | 1/2015 | Burbank et al. |
| 2015/0027951 A1 | 1/2015 | Wallace et al. |
| 2015/0041377 A1 | 2/2015 | Heyes |
| 2015/0076053 A1 | 3/2015 | Higgitt et al. |
| 2015/0129481 A1 | 5/2015 | Higgitt et al. |
| 2015/0196702 A1 | 7/2015 | Burbank et al. |
| 2015/0204733 A1 | 7/2015 | Newell et al. |
| 2015/0238676 A1 | 8/2015 | Giordano et al. |
| 2015/0252800 A1 | 9/2015 | Buckberry et al. |
| 2015/0267821 A1 | 9/2015 | Brugger et al. |
| 2015/0306294 A1 | 10/2015 | Jansson et al. |
| 2015/0359973 A1 | 12/2015 | Onken et al. |
| 2016/0051739 A1 | 2/2016 | Buckberry |
| 2016/0051743 A1 | 2/2016 | Buckberry |
| 2016/0084785 A1 | 3/2016 | Buckberry |
| 2016/0106906 A1 | 4/2016 | Buckberry |
| 2016/0199558 A1 | 7/2016 | Buckberry |
| 2017/0290970 A1 | 10/2017 | Friederichs et al. |
| 2017/0296727 A1 | 10/2017 | Burbank et al. |
| 2017/0296730 A1 | 10/2017 | Soto et al. |
| 2017/0312419 A1 | 11/2017 | Burbank et al. |
| 2017/0326285 A1 | 11/2017 | Hogard et al. |
| 2018/0104400 A1 | 4/2018 | Burbank et al. |
| 2018/0126056 A1 | 5/2018 | Wrazel et al. |
| 2018/0128688 A1 | 5/2018 | Newell et al. |
| 2018/0128698 A1 | 5/2018 | Brugger et al. |
| 2019/0022293 A1 | 1/2019 | Peterson et al. |

FOREIGN PATENT DOCUMENTS

| | | | |
|---|---|---|---|
| CN | 200951223 Y | 9/2007 | |
| DE | 8702995 U1 | 6/1987 | |
| DE | 69217519 T2 | 6/1997 | |
| EP | 0165751 A2 | 12/1985 | |
| EP | 0324922 A2 | 7/1989 | |
| EP | 0679100 A1 | 11/1995 | |
| EP | 0796997 A1 | 9/1997 | |
| EP | 0547025 B2 | 6/2002 | |
| EP | 1892000 A1 | 2/2008 | |
| EP | 2319551 A2 | 5/2011 | |
| EP | 2535067 A1 | 12/2012 | |
| GB | 1289738 A | 9/1972 | |
| JP | 59-58002 | 4/1984 | |
| JP | 60-143803 | 7/1985 | |
| JP | H4-35669 A | 2/1992 | |
| JP | 2002143298 | 5/2002 | |
| JP | 2002527212 A | 8/2002 | |
| JP | 2007268490 A | 10/2007 | |
| JP | 2007529707 A | 10/2007 | |
| JP | 2012152286 A | 8/2012 | |
| JP | WO 2013024825 A1 * | 2/2013 | ............ A61M 1/14 |
| JP | 55-14045 | 6/2014 | |
| WO | WO00/16916 A1 | 3/2000 | |
| WO | WO00/25843 A1 | 5/2000 | |
| WO | WO00/57935 A1 | 10/2000 | |
| WO | WO02/40874 A1 | 5/2002 | |
| WO | WO02/076529 A1 | 10/2002 | |
| WO | WO03/076661 A1 | 9/2003 | |
| WO | WO2006/011009 A2 | 2/2006 | |
| WO | WO2006/039293 A2 | 4/2006 | |
| WO | WO2007/073739 A1 | 7/2007 | |
| WO | WO2007/089855 A2 | 8/2007 | |
| WO | WO2008/027967 A1 | 3/2008 | |
| WO | WO2008/106191 A2 | 9/2008 | |
| WO | WO2010/027435 A1 | 3/2010 | |
| WO | WO2010/062698 A2 | 6/2010 | |
| WO | WO2010/085764 | 7/2010 | |
| WO | WO2010/146343 A2 | 12/2010 | |

(56) References Cited

FOREIGN PATENT DOCUMENTS

| WO | WO2014/117000 A2 | 7/2014 |
|---|---|---|
| WO | WO2014/124180 A2 | 8/2014 |
| WO | WO2014/160370 A1 | 10/2014 |
| WO | WO2015/185920 A1 | 12/2015 |
| WO | WO2016/030147 A1 | 3/2016 |
| WO | WO2016/049542 A2 | 3/2016 |
| WO | WO2016/057981 A1 | 4/2016 |
| WO | WO2016/057982 A1 | 4/2016 |

OTHER PUBLICATIONS

Allis et al., "Chapter 16: Nanostructural Architectures from Molecular Building Blocks," in Handbook of Nanoscience, Engineering, and Technology, 1st Edition (Electrical Engineering Handbook), CRC Press LLC, Boca Raton, FL, Chapter 16 (70 pgs.), Oct. 2002.
Anglés et al., "Plasticized starch/Tunicin Whiskers Nanocomposite Materials. 2. Mechanical behavior," Macromolecules, 34, pp. 2921-2931, Mar. 2001.
California Energy Commission; Development of Supported Polymeric Liquid Membrane Technology for Aqueous MTBE Mitigation, EPRI, Palo Alto, CA, California Energy Commission, Sacramento, CA: Doc. No. 1006577; 70 pgs.; Jul. 2002.
Demura et al., "Ductile Thin Foil of Ni3Al," Mechanical Properties of Structural Films, ASTM International Nov. 2000 Symposium (Orlando, FL), pp. 248-261, published Oct. 1, 2001.
Favier et al.; Nanocomposite materials from latex and cellulose whiskers; Polymers for Advanced Technologies; 6; pp. 351-355; Jan. 1995.
Federal Energy Technology Center, "Technology Development Through Industrial Partnerships," (Tech. Dev. Data Sheet), 12 pgs., Sep. 1998.
Grunert et al., "Progress in the Development of Cellulose Reinforced Nanocomposites," PMSE Preprints 2000, 82, 232, 2 pgs., Mar. 2000.
Haas, "Further development of MMW and SMMW platelet feed horn arrays," Astron. Soc. Pac. Conf. Ser., vol. 75, pp. 99-105, Multi-Feed Systems for Radio Telescopes, Workshop held in Tucson, Arizona, May 16-18, 1994.
Koeneman et al., "Feasibility of Micro Power Supplies for MEMS," (pre-publication copy) J. MicroElectoMechanical Sys., 6(4), pp. 355-362, Dec. 1997.
Morin et al., "Nanocomposites of Chitin Whiskers from Riftia Tubes and Poly (caprolactone)," Macromolecules, vol. 35, pp. 2190-2199, Feb. 2002.
Nakamura et al., "Research on Pressure Welding Conditions of Various Work Metals (Effects of Contact Pressure, Surface Expansion Ratio and Temperature)," JSME International Journal, Series III 31(3), 612-617, Sep. 1988.
Nakao et al., "Diffusion Bonding of Intermetallic Compound TiAl," ISIJ International, 31(10), 1260-1266, Oct. 1991.
Oddy et al., "Electrokinetic Instability Micromixing," Anal. Chern., 73(24), pp. 5822-5832, Dec. 2001.
Omega Engineering Inc.; Load Cell (definition, information); 3 pgs; retrieved from the internet on Jun. 17, 2015 (http://www.omega.com/prodinfo/LoadCells.html).
Orts et al., "Effect of Fiber Source on Cellulose Reinforced Polymer Nanocomposites," ANTEC 2004: Conference Proceedings, 62nd Annual Tech. Conference; Chicago, IL, pp. 2427-2431, May 2004.
Paillet et al., "Chitin Whisker Reinforced Thermoplastic Nanocomposites," Macromolecules, vol. 34, No. 19, pp. 6527-6530, Sep. 2001.
Paul et al., "Microlamination for Microtechnology-based Energy, Chemical, and Biological Systems," ASME IMECE, ASE vol. 39, pp. 45-52, Nashville, Tennessee, Nov. 15-20, 1999.
Pluess, "Application of Controlled Thermal Expansion in Diffusion Bonding for the High-Volume Microlamination of MECS Devices," Thesis (MS), Oregon State University, 193 pgs., Sep. 2004.
Porter et al.; Cost drivers in microlamination based on a high volume production system design; ASME 2002 Conf. Proc.; New Orleans, Louisiana; pp. 267-274; Nov. 17-22, 2002.
Sharma et al., "The Application of Surface Mount Technology to Multi-Scale Process Intensification," ASPE, pp. 1-4, Oct. 2003.
Stroock et al., "Chaotic Mixer for Microchannels," Science, 295, pp. 647-651, Jan. 2002.
Thorsen et al.; Microfluidic Large-Scale Integration; Science; 298; pp. 580-584; Oct. 18, 2002.
Wegeng et al., "Chemical system miniaturization," Proceedings of the AIChE Spring National Meeting, pp. 1-13, Feb. 1996.
Hogard et al.; U.S. Appl. No. 14/699,875 entitled "Dialysis System And Methods" filed Apr. 29, 2015.
Peterson et al.; U.S. Appl. No. 14/808,827 entitled "Fluid Purification System," filed Jul. 24, 2015.
Miller; U.S. Appl. No. 14/827,054 entitled "Through-Plate Microchannel Membrane Devices," filed Aug. 14, 2015.
Hogard et al.; U.S. Appl. No. 14/821,283 entitled "Dialysis system and methods," filed Aug. 7, 2015.
Hogard et al.; U.S. Appl. No. 14/821,307 entitled "Dialysis system and methods," filed Aug. 7, 2015.
Hogard et al.; U.S. Appl. No. 14/821,325 entitled "Dialysis system and methods," filed Aug. 7, 2015.
Hogard et al.; U.S. Appl. No. 14/821,349 entitled "Dialysis system and methods," filed Aug. 7, 2015.
Introtek International; Drip chamber liquid level sensor (sales literature); 2 pages; retrieved from the internet (http://www.introtek.eom/PDFs/1/DDS-14.0_DripDetectSensor.pdf); © Jan. 1, 2009.
Curtis et al.; U.S. Appl. No. 15/225,712 entitled "Dialysis system with ultrafiltration control," filed Aug. 1, 2016.
Hogard et al.; U.S. Pat U.S. Appl. No. 16/295,676 entitled "Dialysis System and Methods," filed Mar. 7, 2019.
Ritson et al.; U.S. Pat Appl. # U.S. Appl. No. 16/325,664 entitled "Peritoneal Dialysis System and Methods," filed Feb. 14, 2019.

* cited by examiner

DIALYSIS SYSTEM AND METHODS

CROSS REFERENCE TO RELATED APPLICATIONS

This application is a continuation of pending U.S. application Ser. No. 14/699,875, filed Apr. 29, 2015, which application claims the benefit of U.S. Provisional Application No. 61/985,779, filed Apr. 29, 2014, titled "Air Removal in Modular Home Dialysis System", and also claims the benefit of U.S. Provisional Application No. 62/127,155, filed Mar. 2, 2015, titled "Dialysis System", both of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to dialysis systems. More specifically, this disclosure relates to dialysis systems that include many features that reduce the need for technician involvement in the preparation and administration of dialysis treatment.

BACKGROUND

There are, at present, hundreds of thousands of patients in the United States with end-stage renal disease. Most of those require dialysis to survive. Many patients receive dialysis treatment at a dialysis center, which can place a demanding, restrictive and tiring schedule on a patient. Patients who receive in-center dialysis typically must travel to the center at least three times a week and sit in a chair for 3 to 4 hours each time while toxins and excess fluids are filtered from their blood. After the treatment, the patient must wait for the needle site to stop bleeding and blood pressure to return to normal, which requires even more time taken away from other, more fulfilling activities in their daily lives. Moreover, in-center patients must follow an uncompromising schedule as a typical center treats three to five shifts of patients in the course of a day. As a result, many people who dialyze three times a week complain of feeling exhausted for at least a few hours after a session.

Many dialysis systems on the market require significant input and attention from technicians prior to, during, and after the dialysis therapy. Before therapy, the technicians are often required to manually install patient blood tubing sets onto the dialysis system, connect the tubing sets to the patient, and to the dialyzer, and manually prime the tubing sets to remove air from the tubing set before therapy. During therapy, the technicians are typically required to monitor venous pressure and fluid levels, and administer boluses of saline and/or heparin to the patient. After therapy, the technicians are often required to return blood in the tubing set to the patient and drain the dialysis system. The inefficiencies of most dialysis systems and the need for significant technician involvement in the process make it even more difficult for patients to receive dialysis therapy away from large treatment centers.

Given the demanding nature of in-center dialysis, many patients have turned to home dialysis as an option. Home dialysis provides the patient with scheduling flexibility as it permits the patient to choose treatment times to fit other activities, such as going to work or caring for a family member. Unfortunately, current dialysis systems are generally unsuitable for use in a patient's home. One reason for this is that current systems are too large and bulky to fit within a typical home. Current dialysis systems are also energy-inefficient in that they use large amounts of energy to heat large amounts of water for proper use. Although some home dialysis systems are available, they generally use complex flow-balancing technology that is relatively expensive to manufacture and most systems are designed with a system of solenoid valves that create high noise levels. As a result, most dialysis treatments are performed at dialysis centers.

SUMMARY OF THE DISCLOSURE

A method of achieving dynamic balancing with a dialysis system is provided, comprising operating a blood pump to move a flow of blood from a patient through a patient tubing set and a blood-side of a dialyzer, operating a first dialysate pump and a second dialysate pump to move a flow of dialysate through a dialysate-side of the dialyzer, bypassing the flow of dialysate through the dialysate-side of the dialyzer, and while the flow of dialysate through the dialysate-side of the dialyzer is bypassed, measuring a dialysate pressure between the first dialysate pump and the second dialysate pump, and adjusting a pump speed of the second dialysate pump until the measured dialysate pressure stabilizes.

In some embodiments, the method further comprises resuming the flow of dialysate through the dialysate-side of the dialyzer.

In other embodiments, no fluid passes from the blood-side of the dialyzer to the dialysate-side of the dialyzer when the flow of dialysate resumes through the dialysate-side of the dialyzer.

A method of achieving dynamic balancing with a dialysis system is also provided, comprising operating a blood pump to move a flow of blood from a patient through a patient tubing set and a blood-side of a dialyzer, measuring a venous pressure of the patient, operating a first dialysate pump and a second dialysate pump to move a flow of dialysate through a dialysate-side of the dialyzer, preventing a flow of dialysate from passing through the dialysate-side of the dialyzer, while the flow of dialysate through the dialysate-side of the dialyzer is prevented, measuring a dialysate pressure between the first dialysate pump and the second dialysate pump, and adjusting a pump speed of the second dialysate pump until the measured dialysate pressure stabilizes, allowing the flow of dialysate to pass through the dialysate-side of the dialyzer, and adjusting a pump speed of the second dialysate pump to create a flow imbalance between the first and second dialysate pumps that results in a flow of fluid between the blood-side of the dialyzer and the dialysate-side of the dialyzer to equalize the flow imbalance.

In one embodiment, the flow of fluid travels from the blood-side of the dialyzer to the dialysate-side of the dialyzer.

In another embodiment, the flow of fluid travels from the dialysate-side of the dialyzer to the blood-side of the dialyzer.

In some embodiments, the method further comprises further adjusting the pump speed of the second dialysate pump to calibrate for a pressure loss between the blood-side of the dialyzer and the dialysate-side of the dialyzer.

In other embodiments, the method further comprises repeating the preventing, measuring, and adjusting steps if the measured venous pressure changes by a predetermined threshold.

In one embodiment, the predetermined threshold comprises more than 30 mmHg.

A dialysis system is provided, comprising a blood pump configured to move a flow of blood from a patient through a patient tubing set and a blood-side of a dialyzer, a venous pressure sensor configured to measure a venous pressure of the patient, a first pump and a second pump configured to control the flow of dialysate through a dialysate-side of the dialyzer, one or more valves configured to bypass the dialysate-side of the dialyzer to prevent the flow of dialysate from passing through the dialysate-side of the dialyzer, a dialysate pressure sensor disposed between the first and second pumps and configured to measure a dialysate pressure when the dialysate-side of the dialyzer is bypassed, and an electronic controller operatively coupled to the blood pump, the venous pressure sensor, the first and second pumps, the one or more valves, and the dialysate pressure sensor, the electronic controller configured to adjust a pump speed of the first and second pumps to create a flow imbalance between the first and second pumps that results in a flow of fluid between the blood-side of the dialyzer and the dialysate-side of the dialyzer to equalize the flow imbalance.

A dialysis system is provided, comprising a dialyzer comprising a blood-side and a dialysate-side, a blood circuit coupled to the blood-side of the dialyzer and further comprising a venous line adapted to be connected to an venous connection site of a patient and an arterial line adapted to be connected to an arterial connection site of the patient, a blood pump coupled to the blood circuit and configured to move blood from the patient, through the arterial line, through the blood-side of the dialyzer, and through the venous line back into the patient, a venous pressure sensor coupled to the blood circuit and configured to measure a venous pressure of the patient, a dialysate circuit coupled to the dialysate-side of the dialyzer and further comprising a dialysate line coupled to a dialysate source, an actuator coupled to the dialysate circuit, the actuator comprising a first configuration in which dialysate moves through the dialysate-side of the dialyzer and a second configuration in which dialysate is prevented from moving through the dialysate-side of the dialyzer, a first dialysate pump and a second dialysate pump coupled to the dialysate circuit and configured to move dialysate from the dialysate source, through the dialysate line, and through the dialysate-side of the dialyzer when the actuator is in the first configuration, a dialysate pressure sensor coupled to the dialysate circuit and configured to measure a pressure of the dialysate between the first dialysate pump and the second dialysate pump, an electronic controller operatively coupled to the blood pump, the venous pressure sensor, the dialysate pressure sensor, the actuator, the first dialysate pump, and the second dialysate pump, the electronic controller being configured to achieve dynamic balancing of fluid flow across the dialyzer during dialysis therapy by performing the steps of adjusting a pump speed of the first dialysate pump to move a flow of dialysate through the dialysate-side of the dialyzer, controlling the actuator to prevent the flow of dialysate from moving through the dialysate-side of the dialyzer, receiving the measured dialysate pressure from the dialysate pressure sensor, and adjusting a pump speed of the second dialysate pump until the measured dialysate pressure stabilizes, controlling the actuator to allow the flow of dialysate to move through the dialysate-side of the dialyzer, and adjusting a pump speed of the second dialysate pump to create a flow imbalance between the first and second dialysate pumps that results in a flow of fluid between the blood-side of the dialyzer and the dialysate-side of the dialyzer to equalize the flow imbalance.

In some embodiments, the electronic controller is configured to receive the measured venous pressure from the venous pressure sensor, and is configured to repeat the controlling, receiving, and adjusting steps if the measured venous pressure changes by a predetermined threshold.

A method of connecting a disposable cartridge and tubing set to a dialysis system is provided, comprising the steps of positioning alignment features of the disposable cartridge and tubing set next to alignment features of the dialysis system, and mounting the disposable cartridge and tubing set onto the dialysis system to acoustically couple a venous drip chamber of the disposable cartridge and tubing set with one or more fluid level sensors of the dialysis system.

In some embodiments, the method further comprises measuring a fluid level within the venous drip chamber with the one or more fluid level sensors.

A disposable cartridge adapted to be mounted onto a dialysis system is provided, comprising a frame having a plurality of alignment features configured to removably mate with corresponding alignment features on the dialysis system, a tubing set disposed in the frame, and a venous drip chamber disposed in the frame and connected to the tubing set, the venous drip chamber being positioned within the frame such that it is acoustically coupled to one or more fluid level sensors of the dialysis system when the frame is mounted onto the dialysis system.

A method of priming a tubing set and a dialyzer of a dialysis system is also provided, comprising the steps of operating a blood pump of the dialysis system in a first operating mode to move saline from a saline source into the tubing set and through a blood-side of the dialyzer in a first direction to remove air from the tubing set and the blood-side of the dialyzer, and operating the blood pump in a second operating mode to move at least a portion of the saline through the blood-side of the dialyzer in a second direction opposite to the first direction and out of the tubing set.

In some embodiments, the method further comprises monitoring a fluid level of the saline in a venous drip chamber of the tubing set, and stopping operation of the blood pump in the first operating mode when the fluid level in the venous drip chamber stabilizes or when air no longer circulates through the tubing set.

In one embodiment, operating the blood pump in the first operating mode further comprises moving at least a portion of the saline into a venous drip chamber of the tubing set before moving the saline through the blood-side of the dialyzer.

In another embodiment, operating the blood pump in the second operating mode further comprises moving at least a portion of the saline through the blood-side of the dialyzer before moving the saline through a venous drip chamber of the tubing set.

In some embodiments, the method further comprises operating a dialysate pump to move dialysate from a dialysate source through a dialysate-side of the dialyzer in the first direction to remove air from the dialysate-side of the dialyzer.

In some embodiments, air is removed from the dialysate-side of the dialyzer without physically manipulating an orientation of the dialyzer.

In other embodiments, air is removed from the dialysate-side of the dialyzer without flipping an orientation of the dialyzer.

In some embodiments, the method further comprises opening one or more valves of the dialysis system with an electronic control to allow the saline to move from the saline source into the tubing set.

In one embodiment, the operating the blood pump steps further comprise operating the blood pump with an electronic controller of the dialysis system.

In other embodiments, the saline is moved out of the tubing set through a union joint that attaches a venous line of the tubing set to an arterial line of the tubing set.

In some embodiments, a predetermined volume of saline is moved through the union joint before the dialysis therapy can begin.

A method of returning blood in a patient tubing set of a dialysis delivery system to a patient after a dialysis treatment is provided, comprising activating a blood pump coupled to the patient tubing set to draw saline into the patient tubing set and push blood back into the patient, tracking the number of revolutions of the blood pump to determine the amount of saline drawn into the patient tubing set, and de-activating the blood pump when a predetermined volume of saline is drawn into the patient tubing set.

In some embodiments, the predetermined volume comprises 300-500 ml.

In some embodiments, the method further comprises opening one or more pinch valves of the dialysis delivery system to create a pathway between a saline source and the tubing set.

In additional embodiments, the method further comprises opening one or more pinch valves to create the pathway between the saline source and the tubing set at or adjacent to a patient arterial access site.

In some embodiments, blood is pushed back into the patient through a patient venous access site.

A method of draining fluid out of a dialyzer of a dialysis system after a dialysis treatment is provided, comprising closing a venous line of a patient tubing set of the dialysis system, and operating a pump coupled to the patient tubing set to pull fluid from a dialysate-side of the dialyzer into a blood-side of the dialyzer and out of the dialyzer into a waste container.

In some embodiments, the waste container comprises a saline bag.

In other embodiments, the fluid is pulled through micro-tube walls of the dialyzer to move the fluid from the dialysate-side of the dialyzer to the blood-side of the dialyzer.

In additional embodiments, the fluid is pulled from the dialyzer against gravity.

A method of controlling a fluid level in a venous drip chamber of a dialysis system during therapy is provided, comprising the steps of generating a flow of blood through a patient tubing set and the venous drip chamber, monitoring a fluid level of the blood in the venous drip chamber with first and second sensors, automatically pumping or venting air out of the venous drip chamber if the fluid level dips below the first sensor, and automatically pumping air into the venous drip chamber if the fluid level rises above the second sensor.

A method of controlling a fluid level in a venous drip chamber of a dialysis system during therapy is provided, comprising the steps of generating a flow of blood through a patient tubing set and the venous drip chamber, monitoring a fluid level of the blood in the venous drip chamber with a sensor, automatically pumping or venting air out of the venous drip chamber if the sensor detects the fluid level dropping below a lower fluid level threshold, automatically pumping air into the venous drip chamber if the sensor detects the fluid level rising above an upper fluid level threshold.

A method of controlling a fluid level in a venous drip chamber of a dialysis system during therapy is provided, comprising the steps of generating a flow of blood through a patient tubing set and the venous drip chamber, monitoring a fluid level of the blood in the venous drip chamber with first and second sensors, and automatically maintaining the fluid level of the blood in the venous drip chamber by pumping or venting air out of the venous drip chamber if the first sensor detects the fluid level dropping below a lower threshold and pumping air into the venous drip chamber if the second sensor detects the fluid level rising above an upper threshold.

A dialysis system is provided, comprising a venous drip chamber configured to remove air from blood flowing therethrough, at least one sensor configured to monitor a fluid level of blood in the venous drip chamber, a pump coupled to the venous drip chamber and configured to pump air into or out of the venous drip chamber, and an electronic controller in communication with the at least one sensor and the pump, the electronic controller configured to automatically control the pump to maintain the fluid level of the blood in the venous drip chamber by pumping air out of the venous drip chamber with the pump when the at least one sensor detects the fluid level dropping below a first threshold and pumping air into the venous drip chamber with the pump when the at least one sensor detects the fluid level rising above a second threshold.

A disposable cartridge adapted to be inserted into a dialysis system for use in dialysis therapy is provided, comprising an organizer having a plurality of aligning holes configured to mate with alignment pegs on the dialysis delivery system, a tubing set disposed in the organizer, the tubing set comprising, an arterial line portion configured to draw blood from a patient, a venous line portion configured to return blood to the patient, a blood pump portion configured to interface with a blood pump of the dialysis delivery system, a first dialyzer portion configured to carry blood to a dialyzer of the dialysis delivery system, a second dialyzer portion configured to return blood from the dialyzer, first and second saline lines configured to couple a saline source to the tubing set, a venous drip chamber disposed in the organizer and configured to remove air from blood entering the venous drip chamber, the venous drip chamber comprising, first and second ports disposed on a lower portion of the venous drip chamber, the first port being coupled to the venous line portion of the tubing set, the second port being coupled to the arterial line portion of the tubing set.

In some embodiments, the disposable cartridge further comprises a heparin line configured to couple a heparin source to the tubing set.

In one embodiment, the heparin line is coupled to a third port disposed on an upper portion of the venous drip chamber.

In another embodiment, the heparin line is coupled to the venous drip chamber at a non-pulsatile location to prevent back streaming of blood into the heparin line during therapy.

In some embodiments, the non-pulsatile location comprises an air gap in the venous drip chamber.

In other embodiments, the first saline line is attached to the tubing set at a proximal end of the blood pump portion of the tubing set.

In additional embodiments, the second saline line is attached to the tubing set near a proximal end of the arterial line portion of the tubing set.

In some embodiments, the disposable cartridge further comprises an arterial pressure pod disposed along the arterial line portion of the tubing set and configured to mate with an arterial pressure sensor of the dialysis delivery system.

In additional embodiments, the disposable cartridge further comprises a venous transducer connection coupled to the venous drip chamber and configured to mate with a venous pressure sensor of the dialysis delivery system.

A dialysis system is provided, comprising a housing, a water purification system disposed in the housing and configured to prepare water for use in dialysis therapy in real-time using an available water source, a dialysis delivery system disposed in the housing configured to prepare dialysate for dialysis therapy, a dialyzer disposed on or in the housing, a front panel disposed on the housing; the front panel comprising, a plurality of alignment features, a venous level sensor, a blood pump, a plurality of pinch valves, an organizer configured to be mounted to the front panel, the organizer including a plurality of mounting features configured to mate with the plurality of alignment features, the organizer comprising, a tubing set disposed in the organizer, the tubing set comprising, an arterial line portion configured to draw blood from a patient, a venous line portion configured to return blood to the patient, a blood pump portion configured to interface with the blood pump, a first dialyzer portion configured to carry blood to the dialyzer, a second dialyzer portion configured to return blood from the dialyzer, first and second saline lines configured to couple a saline source to the tubing set, a venous drip chamber disposed in the organizer and configured to remove air from blood entering the venous drip chamber, the venous drip chamber comprising, first and second ports disposed on a lower portion of the venous drip chamber, the first port being coupled to the venous line portion of the tubing set, the second port being coupled to the arterial line portion of the tubing set, wherein mounting the organizer to the front panel automatically couples the blood pump portion of the tubing set to the blood pump and the venous drip chamber to the venous level sensor.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

This disclosure describes systems, devices, and methods related to dialysis therapy, including a dialysis system that is simple to use and includes automated features that eliminate or reduce the need for technician involvement during dialysis therapy. In some embodiments, the dialysis system can be a home dialysis system. Embodiments of the dialysis system can include various features that automate and improve the performance, efficiency, and safety of dialysis therapy.

In some embodiments, a dialysis system is described that can provide acute and chronic dialysis therapy to users. The system can include a water purification system configured to prepare water for use in dialysis therapy in real-time using available water sources, and a dialysis delivery system configured to prepare the dialysate for dialysis therapy. The dialysis system can include a disposable cartridge and tubing set for connecting to the user during dialysis therapy to retrieve and deliver blood from the user.

Figure 1:
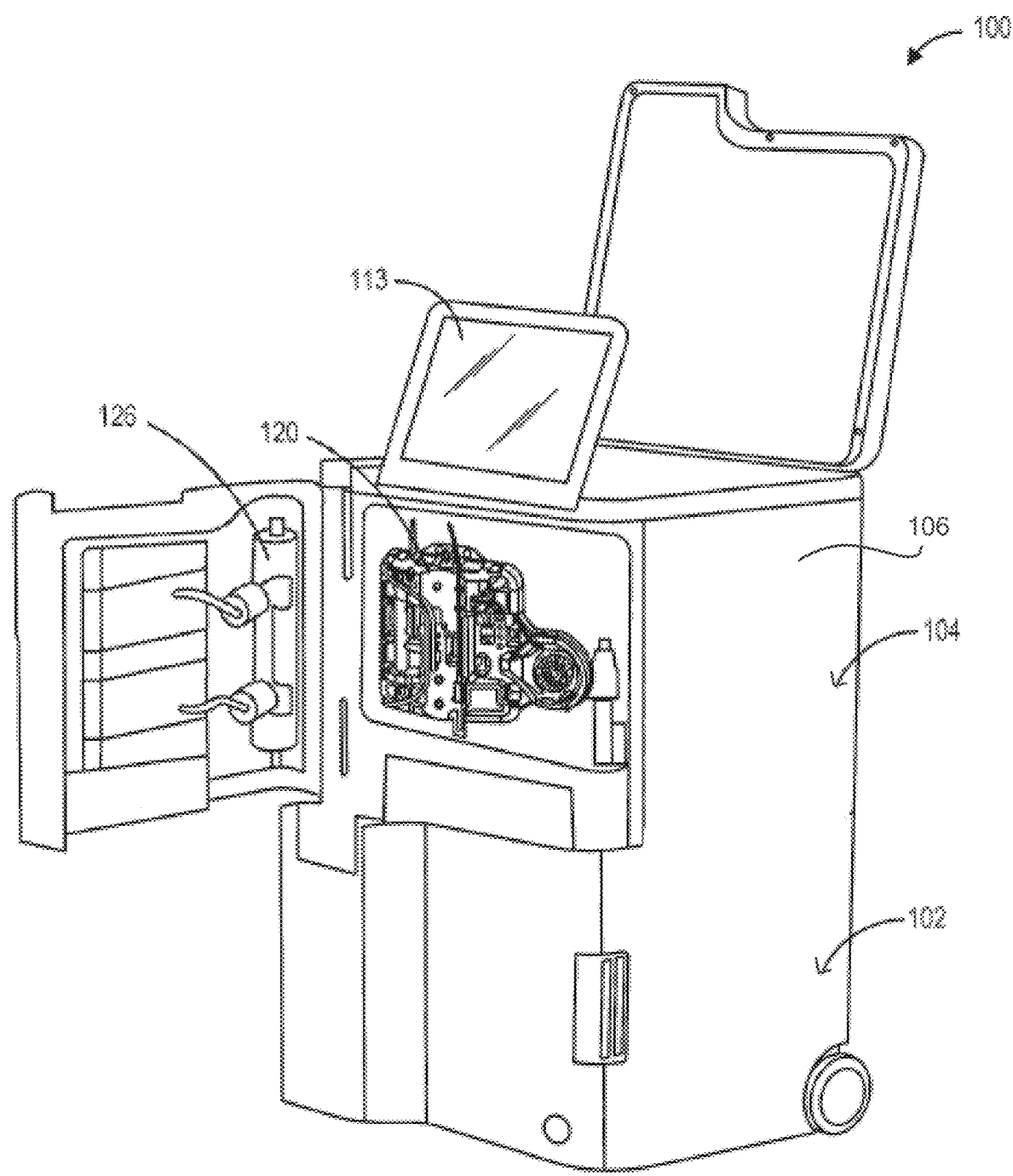
FIG. 1 shows one embodiment of a dialysis system.

FIG. 1 illustrates one embodiment of a dialysis system 100 configured to provide dialysis treatment to a user in either a clinical or non-clinical setting, such as the user's home. The dialysis system 100 can comprise a water purification system 102 and a dialysis delivery system 104 disposed within a housing 106. The water purification system 102 can be configured to purify a water source in real-time for dialysis therapy. For example, the water purification system can be connected to a residential water source (e.g., tap water) and prepare pasteurized water in real-time. The pasteurized water can then be used for dialysis therapy (e.g., with the dialysis delivery system) without the need to heat and cool large batched quantities of water typically associated with water purification methodologies.

Dialysis system 100 can also include a cartridge 120 which can be removably coupled to the housing 106 of the system. The cartridge can include a patient tubing set attached to an organizer, which will be described in more detail below. The cartridge and tubing set, which can be sterile, disposable, one-time use components, are configured to connect to the dialysis system prior to therapy. This connection correctly aligns corresponding components between the cartridge, tubing set, and dialysis system prior to dialysis therapy. For example, the tubing set is automatically associated with one or more pumps (e.g., peristaltic pumps), clamps and sensors for drawing and pumping the user's blood through the tubing set when the cartridge is coupled to the dialysis system. The tubing set can also be associated with a saline source of the dialysis system for automated priming and air removal prior to therapy. In some embodiments, the cartridge and tubing set can be connected to a dialyzer 126 of the dialysis system. In other embodiments, the cartridge and tubing set can include a built-in dialyzer that is pre-attached to the tubing set. A user or patient can interact with the dialysis system via a user interface 113 including a display.

Figure 2:
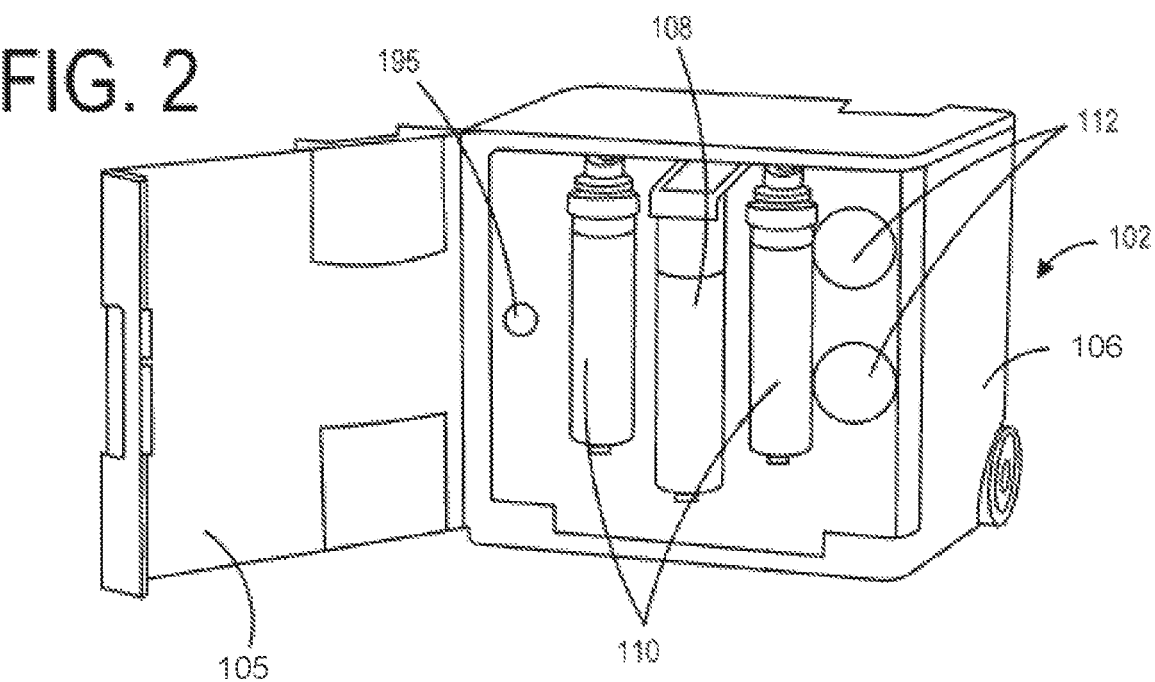
FIG. 2 illustrates one embodiment of a water purification system of the dialysis system.
Figure 3:
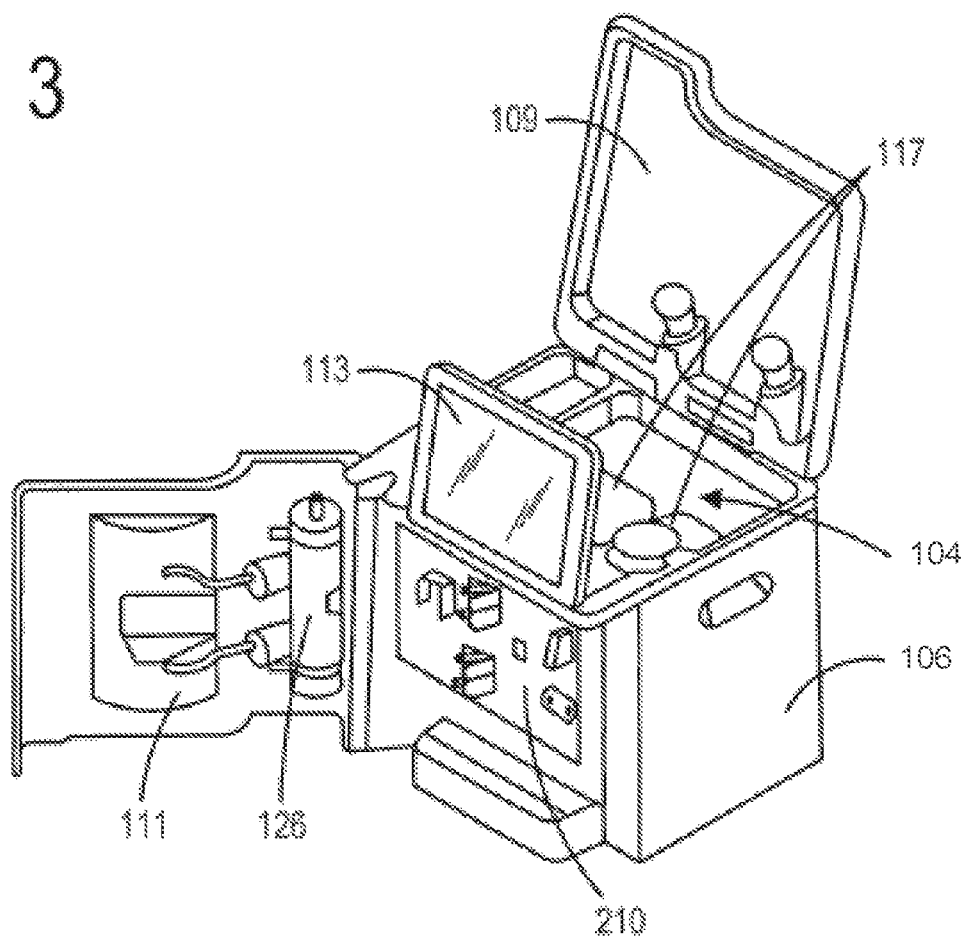
FIG. 3 illustrates one embodiment of a dialysis delivery system of the dialysis system.

FIGS. 2-3 illustrate the water purification system 102 and the dialysis delivery system 104, respectively, of one embodiment of the dialysis system 100. The two systems are illustrated and described separately for ease of explanation, but it should be understood that both systems can be included in a single housing 106 of the dialysis system. FIG. 2 illustrates one embodiment of the water purification system 102 contained within housing 106 that can include a front door 105 (shown in the open position). The front door 105 can provide access to features associated with the water purification system such as one or more filters, including sediment filter(s) 108, carbon filter(s) 110, and reverse osmosis (RO) filter(s) 112. The filters can be configured to assist in purifying water from a water source (such as tap water) in fluid communication with the water purification system 102. The water purification system can further include heating and cooling elements, including heat exchangers, configured to pasteurize and control fluid temperatures in the system, as will be described in more detail below. The system can optionally include a chlorine sample port 195 to provide samples of the fluid for measuring chlorine content.

In FIG. 3, the dialysis delivery system 104 contained within housing 106 can include an upper lid 109 and front door 111, both shown in the open position. The upper lid 109 can open to allow access to various features of the dialysis system, such as user interface 113 (e.g., a computing device including an electronic controller and a display such as a touch screen) and dialysate containers 117. Front door 111 can open and close to allow access to front panel 210, which can include a variety of features configured to interact with cartridge 120 and its associated tubing set, including alignment and attachment features configured to couple cartridge 120 to the dialysis system 100. Dialyzer 126 can be mounted in front door 111 or on the front panel, and can include lines or ports connecting the dialyzer to the prepared dialysate as well as to the tubing set of the cartridge.

In some embodiments, the dialysis system 100 can also include a blood pressure cuff to provide for real-time monitoring of user blood pressure. The system (i.e., the electronic controller of the system) can be configured to monitor the blood pressure of the user during dialysis therapy. If the blood pressure of the user drops below a threshold value (e.g., a blood pressure threshold that indicates the user is hypotonic), the system can alert the user with a low blood pressure alarm and the dialysis therapy can be stopped. In the event that the user ignores a configurable number of low blood pressure alarms from the system, the system can be configured to automatically stop the dialysis therapy, at which point the system can inform the user that return of the user's blood (the blood that remains in the tubing set and dialyzer) back to the user's body is necessary. For example, the system can be pre-programmed to automatically stop therapy if the user ignores three low blood pressure alarms. In other embodiments, the system can give the user a bolus of saline to bring user fluid levels back up before resuming dialysis therapy. The amount of saline delivered to the patient can be tracked and accounted for during ultrafiltration fluid removal.

The dialysis delivery system 104 of FIG. 3 can be configured to automatically prepare dialysate fluid with purified water supplied by the water purification system 102 of FIG. 2. Furthermore, the dialysis delivery system can de-aerate the purified water, and proportion and mix in acid and bicarbonate concentrates from dialysate containers 117. The resulting dialysate fluid can be passed through one or more ultrafilters (described below) to ensure the dialysate fluid meets certain regulatory limits for microbial and endotoxin contaminants.

Dialysis can be performed in the dialysis delivery system 104 of the dialysis system 100 by passing a user's blood and dialysate through dialyzer 126. The dialysis system 100 can include an electronic controller configured to manage various flow control devices and features for regulating the flow of dialysate and blood to and from the dialyzer in order to achieve different types of dialysis, including hemodialysis, ultrafiltration, and hemodiafiltration.

Figure 4:
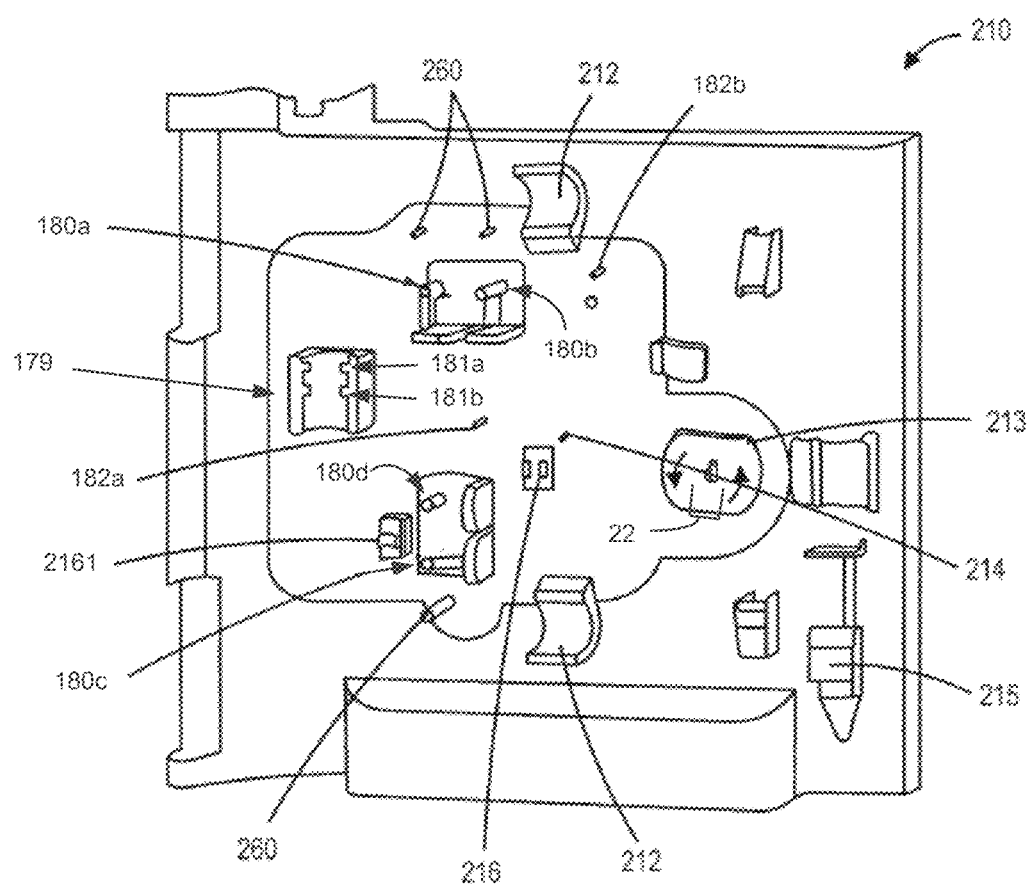
FIG. 4 shows one example of a front panel of the dialysis delivery system.

FIG. 4 shows one example of front panel 210 of the dialysis delivery system 104 of FIG. 3, which can include a number of features that assist with positioning and attaching cartridge 120 and its associated tubing set to the dialysis system 100, and for monitoring and controlling fluid flow along the tubing set of the cartridge. During installation of a new sterile cartridge onto the dialysis system, alignment features on the cartridge (e.g., holes 125 through the cartridge, shown in FIG. 5) can be lined up with locator pegs 260. The locator pegs also serve to align the cartridge and the tubing set with features on the front panel used for dialysis treatment, including blood pump 213 and spring wire 22, positioning features 212, venous and arterial pressure sensor(s) 182a and 182b, venous air sensor 2161, arterial air sensor 216, pinch clamp(s) 180a-d, and venous drip chamber holder 179. Blood pump 213 can be a peristaltic pump, for example. A holder or slot 215 for a heparin pump or syringe is also shown.

The cartridge can be pressed into place on the front panel using these locator pegs 260 to ensure that all the features of the cartridge and tubing set line up and are installed properly with the corresponding features of the front panel 210. In some embodiments, the cartridge can be easily installed with a single hand, and closing the door of the system can seat the cartridge onto the system. As shown in FIG. 1, the dialysis system can include wheels for ease of transport. In one specific embodiment, a force applied to seat the cartridge horizontally onto the front panel 210 by closing the door with a downward rotating motion of a lever on the door does not tend to move the dialysis system 100 on its wheels.

The pinch clamps can be used for a number of functions before, during, and after dialysis therapy. The pinch clamps 180a-d can be controlled by the electronic controller of the dialysis delivery system. Pinch clamps 180a and 180b can be configured to control the flow of saline from a saline source (such as a saline bag) to the tubing set. In some embodiments, the pinch clamps can be opened and the blood pump 213 can be operated to draw saline into the tubing set to remove air during a priming sequence, to flush impurities from the dialyzer before treatment, and to displace blood back to the user at the end of a treatment. The pinch clamps 180a and 180b can also be used to deliver therapeutic boluses of saline to the user during therapy to maintain blood pressure or adjust electrolytes or fluid levels of the patient.

In other embodiments, pumps such as peristaltic pumps may be configured to deliver therapeutic boluses of saline to the user.

Pinch clamps 180c and 180d can be configured to close the arterial and venous lines of the tubing set that connect to the user. They can also be opened and closed multiple times before, during, and after treatment to facilitate actions such as tubing set priming, discarding of priming saline, blood return to the patient, and/or draining the dialyzer after treatment. In one embodiment, the system can incorporate information from venous air sensor 2161, arterial air sensor 216, or other air sensors in the system to close pinch clamps 180c and 180d in the event that air bubbles are found in the lines, particularly in the venous line. In a further embodiment, the system can be configured to remove the detected air bubble(s) by reversing the operation of the blood pump to attempt to clear the air bubble(s) through the venous drip chamber.

Pinch clamps 180a-d can also be actuated to perform a series of self-tests on the tubing set prior to each treatment. The tubing set can be pressurized with the blood pump, and the pressure can be held in the tubing set by closing the pinch valves. The arterial and venous pressure sensors can then be used to look for pressure decay in the tubing set.

FIG. 4 also illustrates venous drip chamber holder 179, which can include a pair of venous level sensors 181a and 181b. When the cartridge is coupled to the dialysis delivery system, the venous drip chamber (described in more detail below) can engage the venous drip chamber holder 179. During dialysis therapy, the venous level sensors 181a and 181b can monitor the fluid level in the venous drip chamber. If the fluid level rises above sensor 181a, then the dialysis delivery system can automatically pump air into the venous drip chamber to lower the fluid level. Alternatively, if the fluid level dips below sensor 181b, then the dialysis delivery system can automatically pump air out of the venous drip chamber (or alternatively, vent air out of the chamber) to raise the fluid level. In other embodiments, the system may comprise a single analog or non-binary digital level sensor in the place of the two venous level sensors to detect the actual level within the drip chamber. The dialysis delivery system can then be configured to perform analogous adjustments as described above based on the level detected by this single sensor. The single sensor can comprise, for example, an ultrasonic, optical, or capacitive level sensor.

Still referring to FIG. 4, in one embodiment, attaching the cartridge onto the front panel 210 properly will engage cartridge presence detector 214, which can be a switch or a sensor configured to communicate to the dialysis system (e.g., to a controller of the system) that a cartridge is installed on the front panel. As a safety precaution, the system will not allow pinch clamps 180a-d to be closed until the cartridge presence detector 214 indicates that the cartridge is installed properly. The presence detector can also initiate automatic loading of a blood pump portion of the tubing set into the blood pump. In one embodiment, the blood pump can include a spring wire 22 that is actuated to grasp and pull the blood pump portion of the tubing set into the blood pump when the presence detector 214 is depressed. Furthermore, the connection of the cartridge and tubing set to the front panel can also initiate a self-check in each portion of the tubing set to identify any leaks in the tubing.

Figure 5:
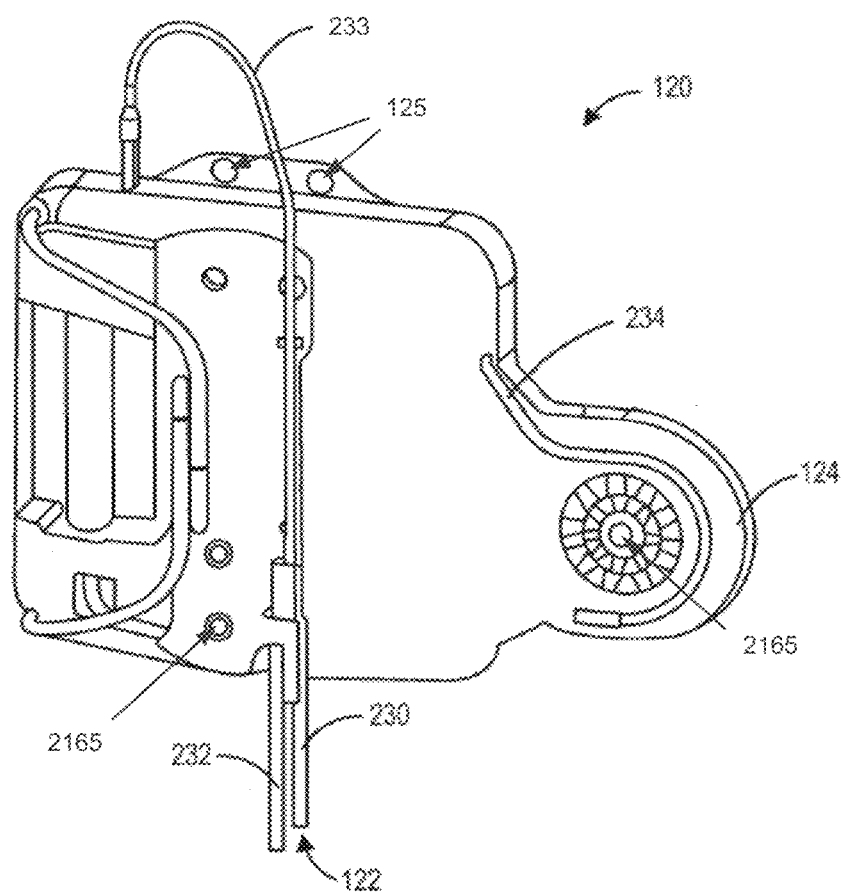
FIGS. 5 and 6 illustrate one embodiment of a cartridge including a tubing set attached to an organizer.
Figure 6:
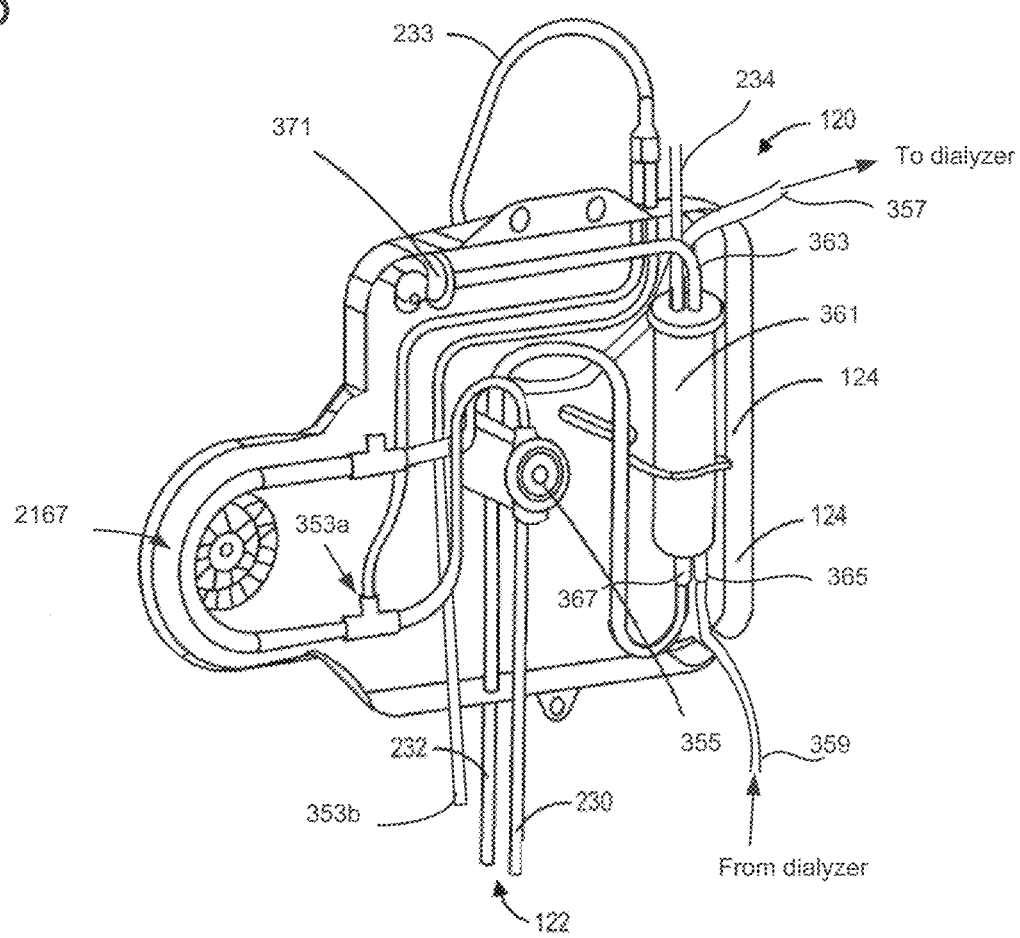

FIGS. 5 and 6 illustrate one embodiment of a cartridge 120 including tubing set 122 attached to an organizer 124. Although the majority of the tubing set 122 is blocked from view in FIG. 5 by the organizer, arterial line 230, venous line 232, saline line 233, and heparin line 234 can be seen. Referring to FIG. 5, a user can ensure proper placement of the cartridge relative to the front panel with organizer 124 by aligning holes 125 of the organizer with the locator pegs 260 of the front panel. FIG. 5 shows a plurality of aligning holes 125 near the top of the organizer, but it should be understood that any number and location of aligning holes and locator pegs can be used to align and mount the cartridge 120. In addition, the organizer 124 can ensure proper placement of the tubing set 122 relative to one or more features of the dialysis system, including valves (such as pinch valves 180a-d described above), sensors (such as pressure and air sensors) the blood pump, the venous drip chamber, etc. Also shown in FIG. 5, the cartridge can include a number of access holes 2165 for gaining access to features on the dialysis delivery system, such as gaining access to pinch valves or the blood pump when the cartridge is installed on the system.

FIG. 6 shows the back side of the cartridge 120 and organizer 124 which is configured to interface with the front panel 210 of the dialysis delivery system, including the tubing set 122. The tubing set 122 of the cartridge 120 can include an arterial line 230, a venous line 232, and a blood pump portion 2167 configured to interface with the blood pump 213 on the front panel 210. The blood pump 213 can be configured to draw blood from a user through arterial line 230, pass the blood through a dialyzer, and return the treated blood to the patient through venous line 232. The tubing set 122 can also be connected to venous drip chamber 361 for the removal of air from the lines during therapy and priming. A continuous pathway through which blood can circulate and dialyze can be created by connecting one end of the arterial line 230 and one end of the venous line 232 of the tubing set 122 to the user's blood vessels, such as via an access point (e.g., fistula needles or catheter). Opposite ends of the arterial and venous lines can be attached to the dialyzer (described below), such as via color coded connectors (e.g., red for arterial and blue for venous).

The tubing set can further include saline connections 353a and 353b to a saline solution, such as a saline bag, via a saline line 233. As shown in FIG. 6, saline connection 353a can connect to the tubing set proximal to the blood pump portion of the tubing set. Tubing set 353b can exit the cartridge and connect to the tubing set on arterial line 230 near where the arterial line is connected to the user. Connecting the saline connection 353b near the arterial connection to the user improves blood return after a dialysis treatment since all the blood in the arterial line can be flushed back into the user. The tubing set can also include a connection to a heparin pump or syringe via the heparin line 234. The heparin pump and heparin line can connect to the tubing set at a non-pulsatile location, such as at the top of the venous drip chamber, to prevent back-streaming of blood up into the heparin line. The connection at the top of the venous drip chamber can be a non-pulsatile location due to the air gap created between the heparin line and fluid in the venous drip chamber.

Flow of fluid, such as blood, through the tubing set 122 will now be described. As described above, the blood pump that interacts with blood pump portion 2167 of tubing set 122 can be a peristaltic pump. The blood pump can operate in two modes of operation. One mode of operation can be a "forward" operating mode of the blood pump that can be used during dialysis therapy to move blood from the patient into the tubing set and back to the patient. Another mode of operation can be a "reverse" operating mode of the blood pump that can be used during a priming sequence to move saline through the tubing set. Fluid flows through the tubing set in the "forward" operating mode in a direction opposite to fluid flowing through the tubing set in the "reverse" operating mode. During dialysis therapy, blood can be drawn from the patient into the tubing set 122 through arterial line 230, due to the blood pump 213 interacting with the tubing set in the "forward" operating mode. Arterial pressure pod 355 can mate with a pressure sensor (arterial pressure sensor 182*b* of FIG. 4) or transducer on the front panel of the dialysis delivery system to measure the pressure on the arterial line during therapy. The arterial pressure pod 355 comprises a diaphragm that allows for pressure to be transmitted without the transmission of blood into the system. The blood can continue through the tubing set, past saline connection 353*a* and through the blood pump portion of the tubing set, and through tubing portion 357 towards the dialyzer. Once the blood has traveled through the dialyzer, it can continue in the tubing set 122 through tubing portion 359 back into the cartridge, where it enters venous drip chamber 361 at the bottom of the drip chamber at entry port 365. Blood flows into the venous drip chamber 361, where air is separated from the blood into the venous drip chamber and removed from the system (e.g., such as from a vent or port at the top of the drip chamber). The venous drip chamber can be connected to a venous pressure sensor or transducer on the dialysis delivery system via line 363 and venous transducer protector 371, which prevents blood or other fluids from contaminating the pressure sensor. Blood that has entered the venous drip chamber can then exit the chamber via exit port 367 and continue to flow through the tubing set until it is returned to the patient through venous line 232.

As shown in FIG. 6, the venous drip chamber includes entry and exit ports 365 and 367 that allows blood to enter and exit the venous drip chamber from the bottom of the venous drip chamber. Any air bubbles caught in the line or the blood percolate into the chamber and are removed from the blood before it is returned to the patient. This configuration allows for fluid flow through the tubing set to be reversed during priming of the dialyzer to push air up and out of the dialyzer. It also allows for the flow of blood to be reversed in the tubing set in the event that air is detected in the venous line of the tubing set.

Figure 18:
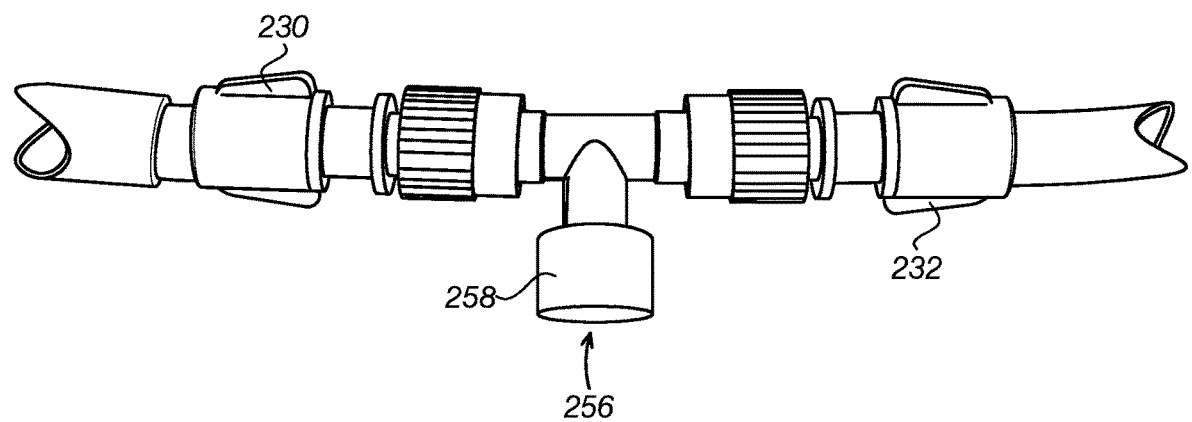
FIG. 18 shows one embodiment of a union joint adapted to connect venous and arterial lines of a patient tubing set during a priming sequence.

Before treatment, the tubing set can be primed with saline to remove air from the line and prepare the system for dialysis therapy. During a priming sequence, the arterial and venous lines of the tubing set can be connected together to form a continuous loop in the tubing set. FIG. 18 shows one embodiment of a union joint 256 configured to attach arterial line 230 to venous line 232.

Saline can be drawn into the tubing set through saline connections 353*a* and/or 353*b* by activating the blood pump in the "forward" and "reverse" operating modes to cause the blood pump to interact with the tubing set and move saline into the tubing set from the saline source. When the pump operates in this "reverse" operating mode, the saline moves from the saline source into the tubing set and the blood-side of the dialyzer to fill the tubing set and the dialyzer with fluid and remove air from the tubing set via the venous drip chamber. In this "reverse" operating mode, saline flows through the tubing set in the opposite direction of blood flow during dialysis therapy. Thus, the saline flows through the venous drip chamber before flowing through the blood-side of the dialyzer. Air in the venous drip chamber can be monitored with the venous level sensors. Any air in the system can be pushed by the saline into the venous drip chamber.

When the venous level sensors no longer detect any changes to the fluid level in the venous drip chamber, or when air sensors no longer detect air circulating through the tubing set, then the tubing set is primed and ready for treatment. The blood pump can then be operated in the "forward" operating mode to move the saline in the other direction than described above and out of the tubing set. In the "forward" operating mode, the saline travels through the blood-side of the dialyzer before passing through the venous drip chamber and into the patient through venous line 232. In some embodiments, the saline used during the priming sequence is delivered into the patient at the start of dialysis therapy. The amount of saline delivered is tracked and accounted for during dialysis therapy depending on the patient's individual fluid removal requirements. In another embodiment, some or all of the saline is pumped or drained out of the tubing set prior to therapy.

To complete the priming sequence, dialysate can be pumped or moved through the dialysate-side of the dialyzer with a dialysate pump (described below). The dialysate is pumped through the dialysate-side of the dialyzer in the same direction that saline is pumped through the blood-side of the dialyzer. The direction of the saline and dialysate through the dialyzer can be in the direction of bottom to top through the dialyzer, which allows the bubbles to naturally purge through the top of the dialyzer. Thus, the priming sequence of the present disclosure can remove air from both the blood-side and dialysate-sides of the dialyzer without physically manipulating or "flipping" an orientation of the dialyzer, as is required by other conventional systems, since the priming sequence moves fluid through both sides of the dialyzer in the same direction.

During therapy, blood in the tubing set normally passes through the blood-side of the dialyzer in the top down direction. However, during priming, the blood pump can be operated in the "reverse" direction to push saline through the dialyzer in the bottom to top direction to more effectively remove air from the dialyzer. The unique configuration of the tubing set and venous drip chamber allows for the flow of saline in the "reverse" direction through the tubing set because fluid both enters and exits the venous drip chamber at connections on the bottom of the venous drip chamber. Conventional venous drip chambers, in which tubing connections are made at the top and bottom of the venous drip chamber, only allow for fluid flow through the venous drip chamber in one direction. The unique configuration of this disclosure allows for priming of both the blood and dialysate sides of the dialyzer without having to physically flip the dialyzer. Any air generated in the venous drip chamber during priming can be removed by either venting out of the system, or pumping out of the system. In one embodiment, the pinch valves of the system can be periodically actuated to open and close the saline lines of the tubing set depending on the timing of the priming sequence to "bang" bubbles loose in the dialyzer. For example, the pinch valves can be opened and closed every 4-8 seconds to create a pulsing effect of the saline in the lines.

After a priming sequence when saline is in the tubing set, the system can further run self-tests to check for leaks in the tubing set. In one embodiment, the pinch valve on the venous line can be closed with the blood pump running, and air can be pumped into the venous drip chamber. Next, the arterial pinch valve can be closed, and the venous pinch valve can be opened, and the system can check for pressure stabilization. If there is no pressure decay, it can be confirmed that there are no leaks in the system.

At the completion of a dialysis treatment, blood still remains inside the tubing set. The blood pump 213 can be controlled to draw saline into the tubing set to push the remaining blood back into the patient. This blood return mechanism can be highly controlled by the controller and blood pump of the system. For example, during dialysis therapy and blood return, the controller of the system can monitor and track the exact number of revolutions made by the blood pump when the pinch valves that control saline administration are open to know exactly how much saline has been pushed into the tubing set. The blood pump can then be stopped or de-activated when the desired volume of saline is drawn into the tubing set. This allows the system to know exactly how much saline has been used, and how much remains in the saline source or bag. At the end of the dialysis therapy, the amount of blood in the tubing set is known (typically around 250 ml), so the system can precisely meter the correct amount of saline into the tubing set to push the blood back into the user. The anticipated amount of saline to use for blood return (typically 300-600 ml depending on the varying degree of thoroughness of the blood return) can be integrated into the overall fluid removal target for ultrafiltration so that after the blood return the patient target weight is attained. If the needed amount of saline does not remain in the saline source prior to blood return, the system can alert the user that the saline source needs to be refilled or replaced.

In one embodiment, the dialyzer can be flushed prior to beginning dialysis therapy with a patient. In some cases, clinics ignore this labeling and do not flush the dialyzer. The system can be configured to flush the dialyzer with up to 500 ml of saline. As described above, the tubing set is filled with saline during the priming sequence. During this priming, the arterial and venous lines are attached to each other with union joint 256 as illustrated in FIG. 18. After the tubing set is primed, the patient can remove cap 258 from the union joint 256 and position the union joint over a waste bucket. The dialysis system can then be placed into a prime discard sequence, which first confirms that valves 180b and 180c (from FIG. 17) are closed, and that valves 180a and 180d (from FIG. 17) are open. The blood pump can be operated in a forward direction to draw saline into the tubing set until the desired prime discard amount is pumped through the system and drained though the union joint 256 of FIG. 18. Next, valve 180d is closed, valve 180C is opened, and the saline is allowed to be gravity drained through the union joint until the proper amount of saline feeds out of the union joint (e.g., 40 ml of saline in one embodiment).

The system can also automatically drain any fluid out of the dialyzer after a dialysis treatment. In one embodiment, the blood pump can be run in the reverse direction with the venous line clamped to pull fluid from the dialysate chamber of the dialyzer through the dialyzer microtube walls against gravity through the dialyzer and into the saline source or bag.

Figure 7:
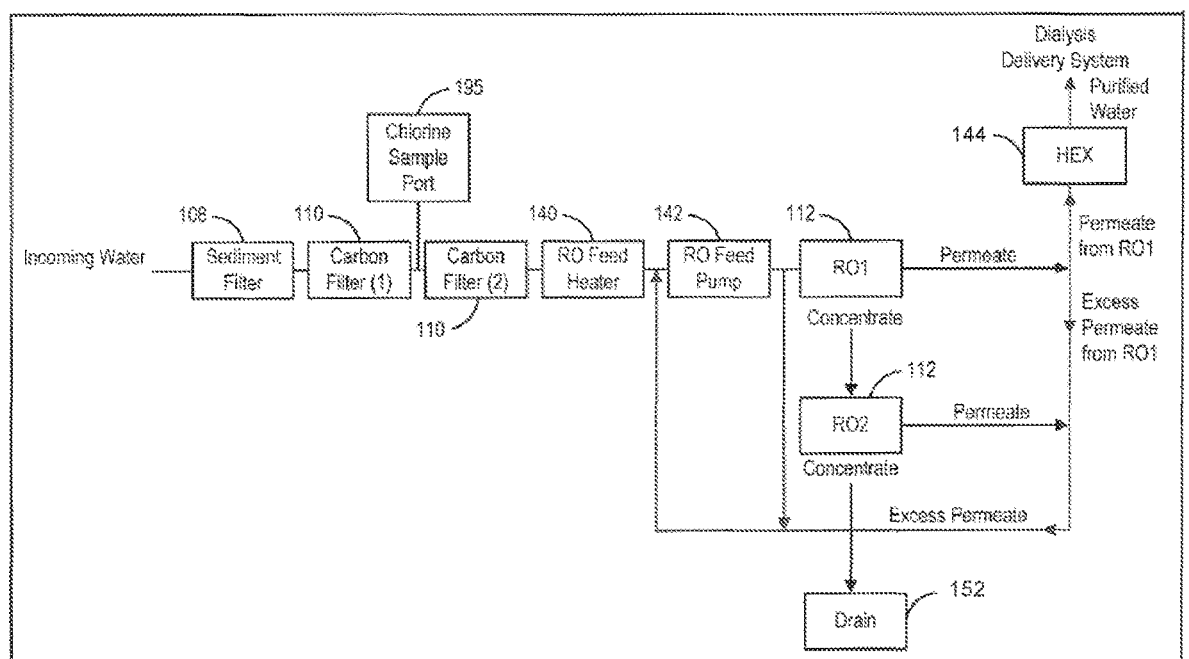
FIG. 7 shows a flow diagram of the water purification system contained within the dialysis system.

FIG. 7 shows a flow diagram of the water purification system 102 contained within the dialysis system 100. Incoming water, such as from the tap, can flow through a number of filters, including one or more sediment filters 108 and one or more carbon filters 110. A chlorine sample port 195 can be placed between the carbon filters 110 to provide samples of the fluid for measuring chlorine content. Redundant or dual carbon filters can be used to protect the system and the user in the event of a carbon filter failure. The water can then pass through a reverse osmosis (RO) feed heater 140, a RO feed pump 142, one or more RO filters 112 (shown as RO1 and RO2), and a heat exchanger (HEX) 144. Permeate from the RO filters 112 can be delivered to the HEX 144, while excess permeate can be passively recirculated to pass through the RO feed pump and RO filters again. The recirculation helps with operating of the water purification system by diluting the incoming tap water with RO water to achieve higher rejection of salts from incoming water. After passing through the HEX 144, the purified water can be sent to the dialysis delivery system 104 for preparing dialysate and assisting with dialysis treatments. Additionally, concentrate from the RO filters during the water purification process can be sent to drain 152.

Figure 8:
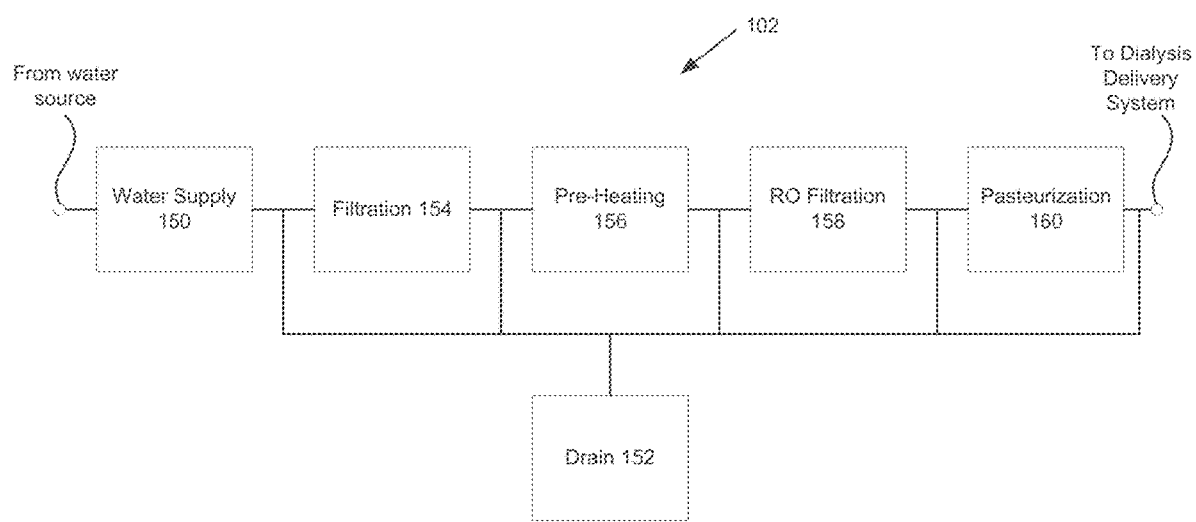
FIG. 8 is a schematic diagram showing a water supply subsystem, a filtration subsystem, a pre-heating subsystem, an RO filtration subsystem, and a pasteurization subsystem of the water purification system of the dialysis system.

Referring to FIG. 8, the water purification system 102 of the dialysis system can include one or more subsystems as described above in FIG. 7, including a water supply subsystem 150, a filtration subsystem 154, a pre-heating subsystem 156, an RO filtration subsystem 158, and a pasteurization subsystem 160. Each of the subsystems above can produce output to a drain 152. The water purification system 102 can be configured to purify a water source in real-time for dialysis therapy. For example, the water purification system can be connected to a residential water source (e.g., tap water) and prepare pasteurized water in real-time. The pasteurized water can then be used for dialysis therapy (e.g., with the dialysis delivery system) without the need to heat and cool large batched quantities of water typically associated with water purification methodologies.

Figure 9:
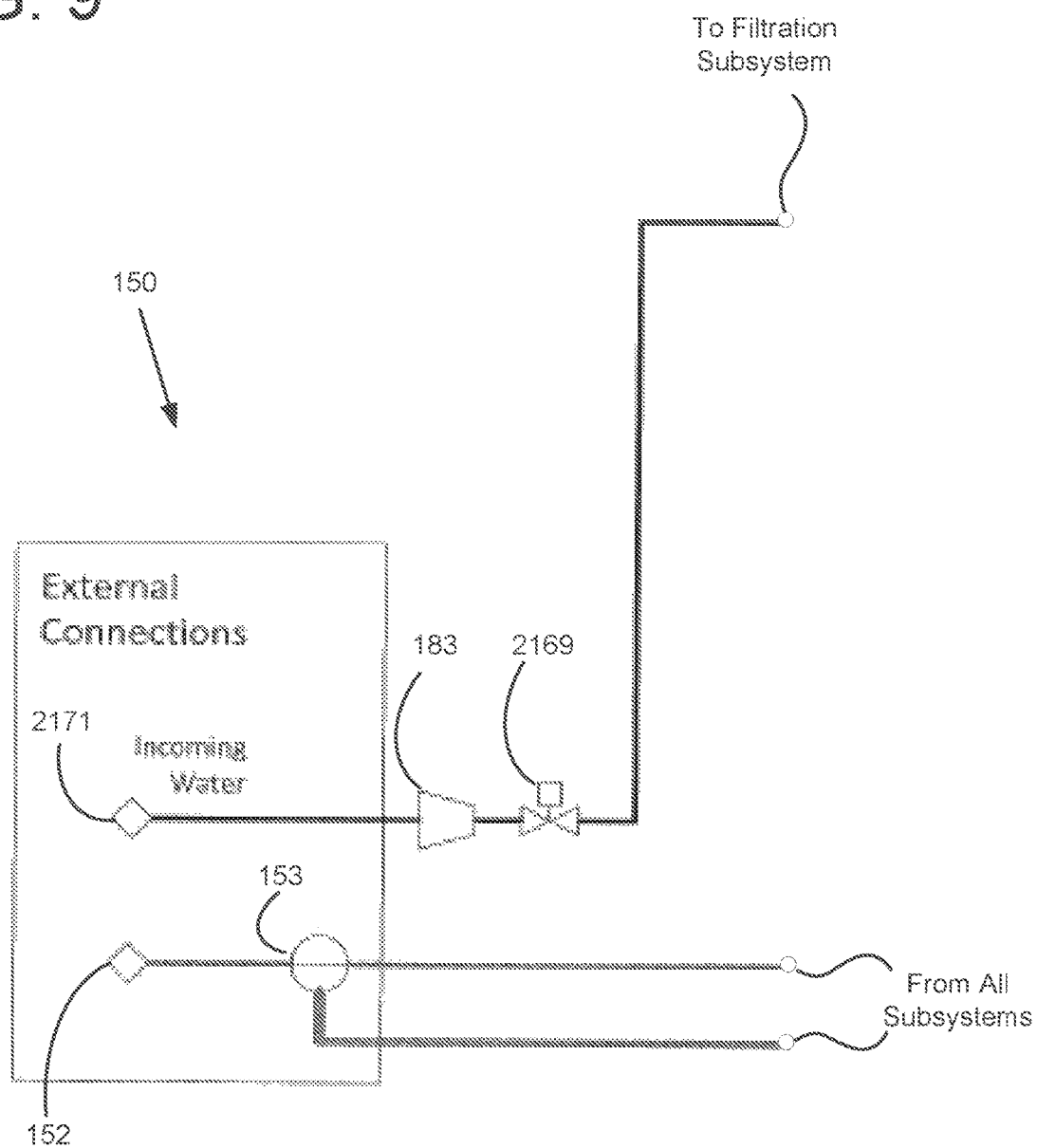
FIG. 9 shows the features of the water supply subsystem of the water purification system.

FIG. 9 shows the features of the water supply subsystem 150 of the water purification system, which can include a variety of valves (e.g., three-way valves, control valves, etc.) for controlling fluid flow through the water purification system. For example, at least one valve 2169 can be opened to allow water to flow into the water purification system for purification. The incoming water can flow in from a tap water source 2171, for example. Fluid returning from the water purification system can be directed to drain 152 through one or more of the valves. Furthermore, the subsystem can include a supply regulator 183 that can adjust the water supply pressure to a set value. A drain pressure sensor 153 can measure the pressure at the drain. Water can flow from the water supply subsystem 150 on to the filtration subsystem, described next.

Figure 10:
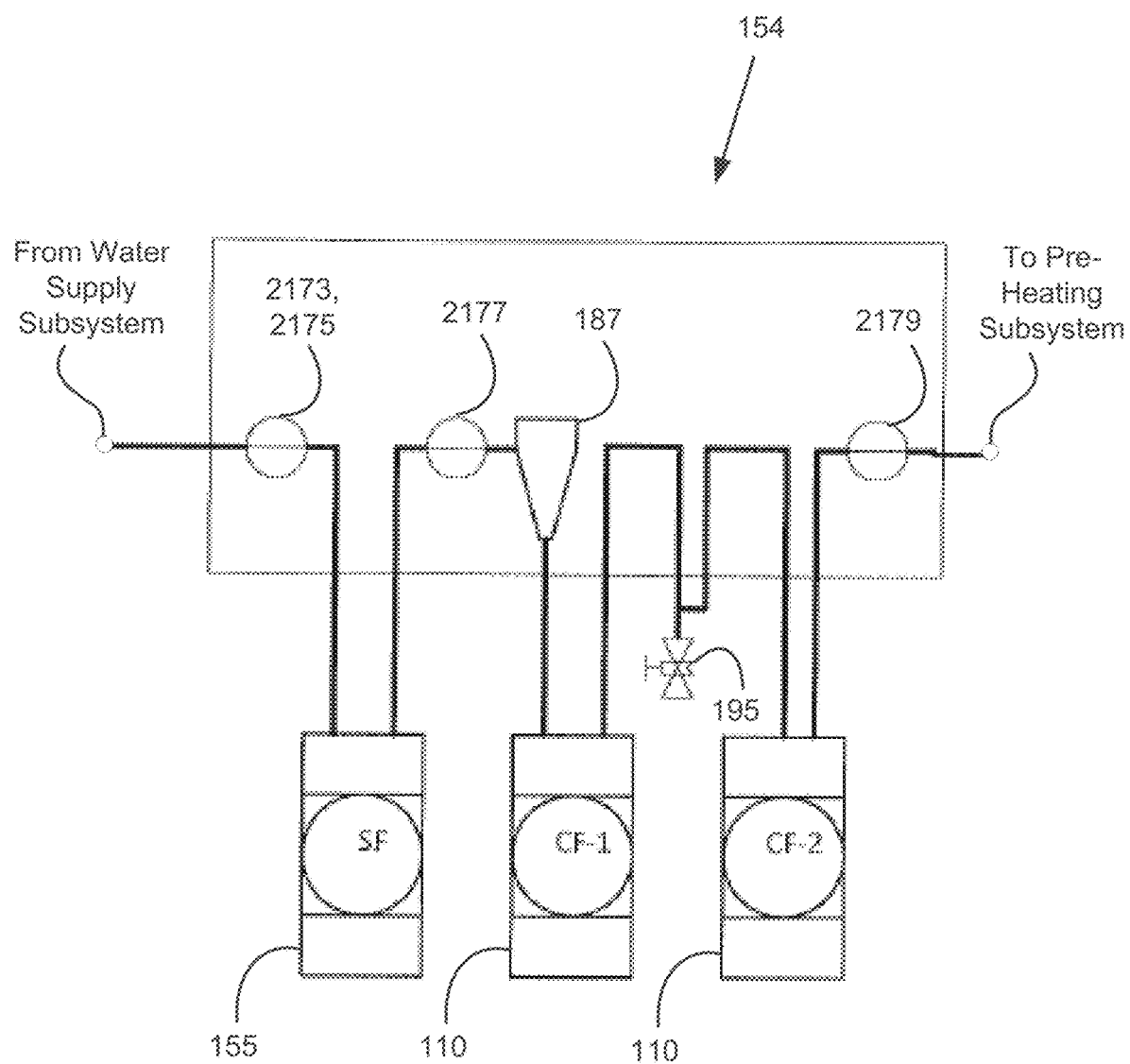
FIG. 10 shows one embodiment of a filtration subsystem of the water purification system.

FIG. 10 shows one embodiment of a filtration subsystem 154 of the water purification system. The filtration subsystem can receive water from the water supply subsystem 150 described in FIG. 9. Water can first pass through a supply pressure sensor 2173 configured to measure the water pressure and a supply temperature sensor 2175 configured to sense the temperature of the incoming water supply. The filtration subsystem can include a sediment filter 155, for example, a 5-micron polypropylene cartridge filter. The filter typically requires replacement every 6 months. Based on the high capacity of the sediment filter and the relatively low flow rate through the filter, the life expectancy is estimated to be over 1 year based on the average municipal water quality in the US. A replacement interval of 6 months provides high assurance that premature sediment filter fouling should be rare. Also, expected to be a rare occurrence based on the construction and materials of the filter is a failure that results in unfiltered water passing through the filter. A post-sediment pressure sensor 2177 can measure the pressure drop across the sediment filter to monitor and identify when the sediment filter needs to be replaced. Should the sediment filter allow unfiltered water to pass the result would be fouling of the carbon filters which would be detected by a pressure drop at post-sediment pressure sensor 2177. If this pressure drop is the significant factor when the sensor drops to 5 psig, the system will require replacement of both the carbon filters and the sediment filters prior to initiating therapy.

The water can then flow through one or more carbon filters 110 (shown as CF-1 and CF-2) configured to filter materials such as organic chemicals, chlorine, and chloramines from the water. For example, the carbon filters 110 can include granulated carbon block cartridges having 10-micron filters. The carbon filters can be connected in series with a chlorine sample port 195 positioned in the flow path between the carbon filters. The chlorine sample port can provide a user with access (such as through the front panel of the system) to the flowing water such as for quality control purposes to ensure the total chlorine concentration level of the water is below a certain threshold (e.g., below 0.1 ppm). Additionally, a post-carbon pressure sensor 2179 can be placed after the carbon filter(s) to monitor the fluid pressure in the line after the sediment and carbon filtration. As is also shown in FIG. 10, an optional air separator 187 can be placed between the sediment filter and the carbon filter(s) to remove excess air and bubbles from the line. In some embodiments, each carbon filter can specified to have a service life of 2500 gallons producing water that has less than 0.5 ppm of free chlorine and chloramine when operating in high chlorine conditions and at a higher flow rate than the instrument supports so an expected life of greater than 2500 gallons is expected. Based on a maximum treatment flow rate of 400 mL/min through the carbon filters the expected for a single carbon filter is approximately 6 months to a year or more depending on incoming water quality. The system typically requires replacement of both filters every 6 months. Most carbon filters cannot tolerate heat or chemical disinfection, therefore a recirculation/disinfection fluid path, implemented by the water supply and drain systems, does not include the carbon filters (or the sediment filters). Since the chlorine absorption capacity of carbon filters is finite and dependent on the incoming water quality, a water sample from the chlorine sample port 195 can be taken to verify that the water has a free chlorine concentration level of less than 0.1 ppm. Using the two stage carbon filtration and verifying the "equivalent absence" of free chlorine after the first carbon filter ensures that the second carbon filter remains at full capacity in complete redundancy to the first. When the first carbon filter does expire, both filters are typically replaced. Water can flow from the filtration subsystem to the pre-heating subsystem, described next.

Figure 11:
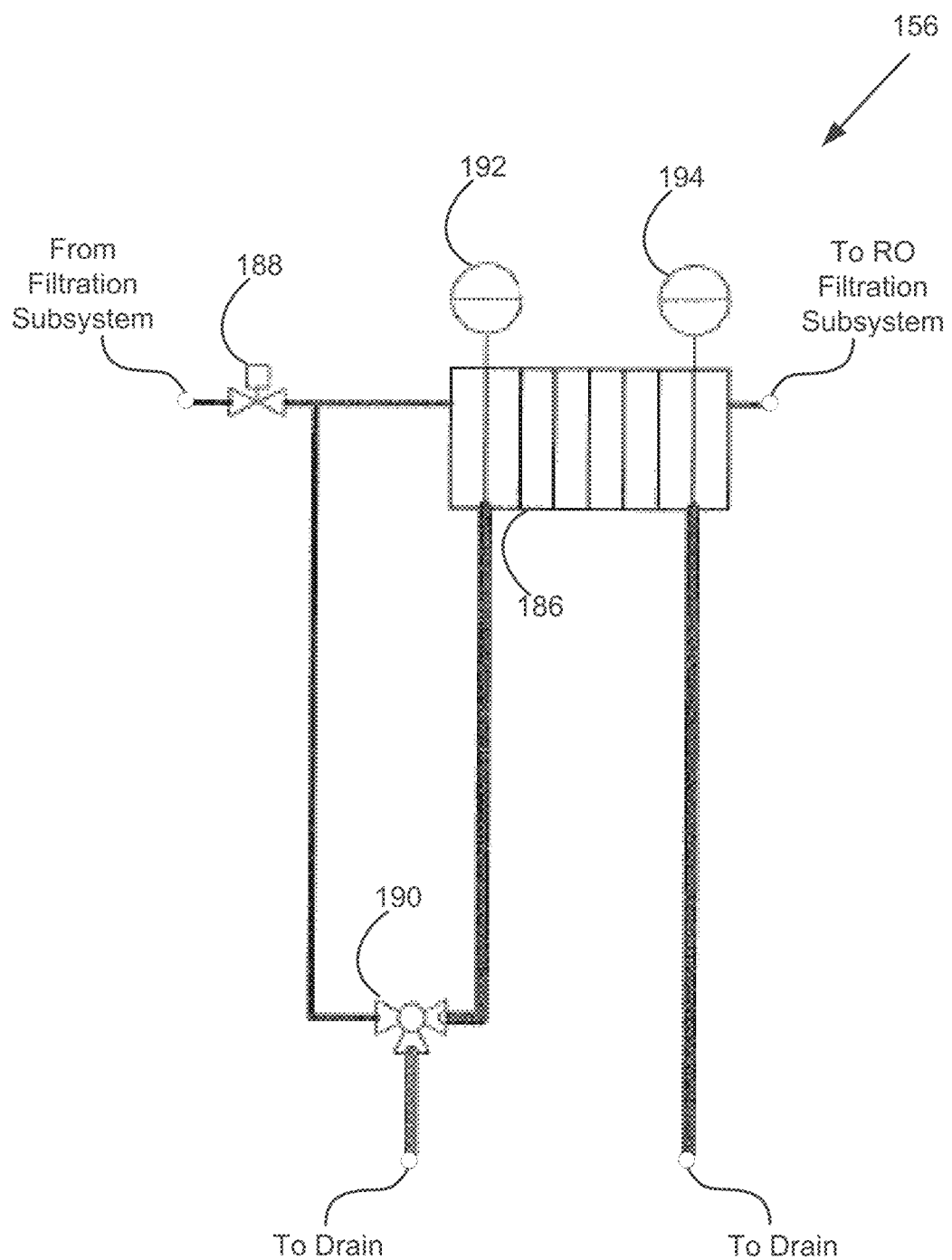
FIG. 11 shows one embodiment of a pre-heating subsystem of the water purification system.

FIG. 11 shows one embodiment of a pre-heating subsystem 156 of the water purification system. The pre-heating subsystem can be configured to control the temperature of water in the line to optimize RO filtration performance. The pre-heating subsystem can include one or more RO feed heaters 186, which can comprise, for example a thermoelectric device such as a Peltier heater/cooler. The RO feed heater 186 can be configured to regulate or adjust the temperature of the water before RO filtration. In one embodiment, the target temperature for reverse osmosis is 25 degrees C. for optimal RO filter performance. If the water is too cold the RO filters will have insufficient flow and the system will not make enough water. If the water is too warm the RO filters will allow more flow but also have reduced salt rejection. In one embodiment, 25° C. is the point at which flow and rejection are balanced to provide sufficient water volume with adequate rejection. The RO feed heater can be used to both heat or cool the fluid flowing through the heater. For example, in some embodiments, the RO feed heater can recover heat from waste water or used dialysate by way of the Peltier effect. In other embodiments, such as during a heat disinfect cycle, the RO feed heater can be placed in opposing polarity to negate Peltier effects. During water treatment, the incoming water flows through a titanium plate attached to the hot side of two thermoelectric wafers of the RO feed heater. Waste water can be directed through a separate titanium plate attached to the cold side of the wafers. Heat is therefore pumped from the waste water to the incoming water via the Peltier effect. At maximum power when the preheating system achieves a coefficient of performance of two, meaning half of the power heating the incoming water is recovered from waste water and the other half is from the electrical heating of the wafers. At lower power levels the coefficient of performance is higher meaning a higher percentage of the heat is recovered from the waste stream. During heat disinfect the thermoelectric wafers of the RO feed heater can be placed in opposing polarity. In this way both titanium plates are heated and the Peltier effect is negated. This ensures that the water is heated only and is always above the incoming temp on either side of the heater.

As shown in FIG. 11, the pre-heating subsystem 156 can include a process supply valve 188 in the line between the filtration subsystem and the RO feed heater, and a used dialysate return valve 190 for routing used dialysate to the drain. The RO feed heater can include a pair of temperature sensors 192 and 194 to measure the temperature of the fluid on either side of the heater. Water can flow from the pre-heating subsystem to the RO filtration subsystem, described next.

Figure 12:
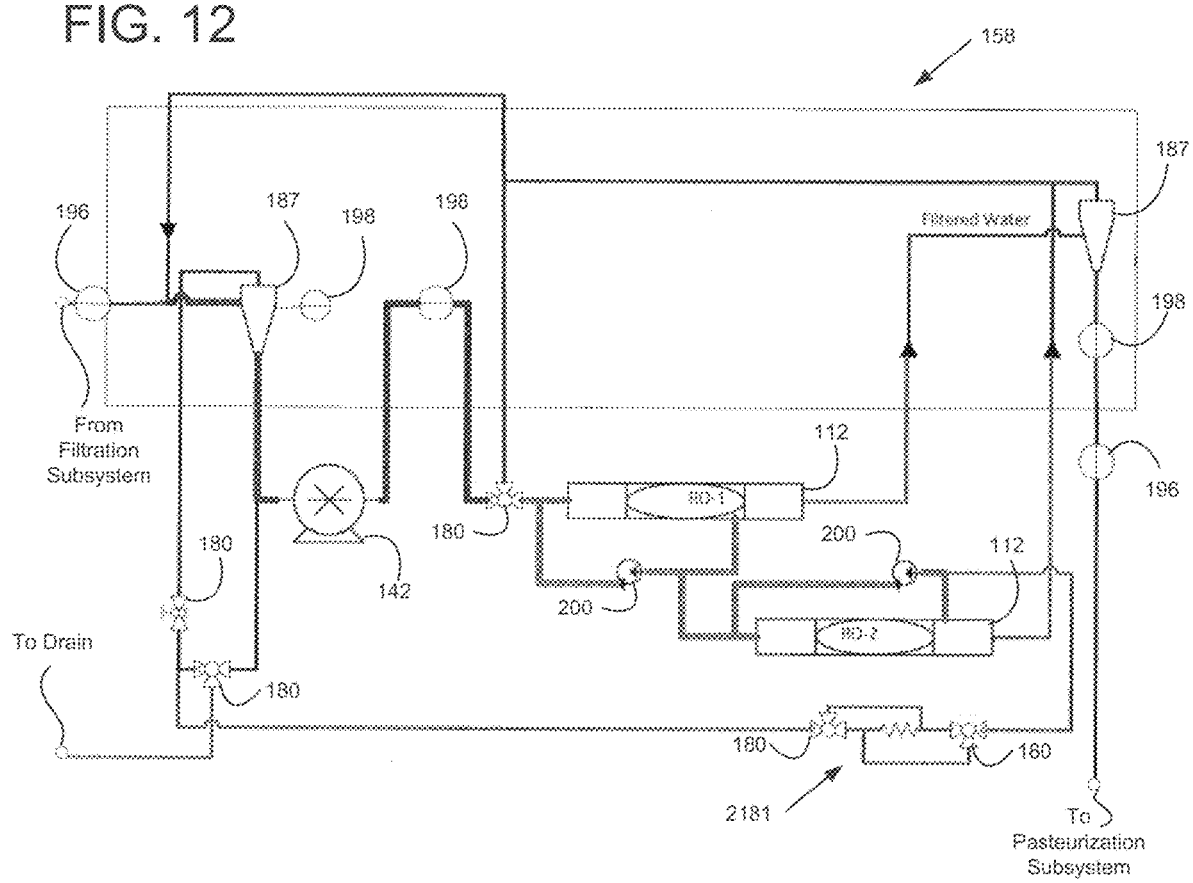
FIG. 12 shows one embodiment of a RO filtration subsystem of the water purification system.

FIG. 12 shows one embodiment of a RO filtration subsystem 158 of the water purification system. The RO filtration subsystem can receive pre-heated water from the pre-heating subsystem described above. The RO filtration subsystem can include a RO feed pump 142 that can drive water across one or more RO filters 112 (shown as RO-1 and RO-2) to produce a permeate flow and a concentrate flow. The concentrate flow can be filtered by more than one RO filter. In addition, the permeate flow can be combined with excess permeate and be recirculated back to blend with incoming water. In addition, each RO filter 112 can include a recirculation pump 200 to keep fluidic line flow velocity high over the RO filters. The recirculation pumps can run at a constant velocity, driving any flow emanating from the concentrate flow back into the inlet of the RO filters. Using a separate recirculation pump instead of recirculating through the RO feed pump lowers overall power consumption and keeps flow velocity over the RO membranes high to reducing fouling and allow for high water production rates. In some embodiments, the RO feed pump can be high pressure but relatively low flow pumps compared to the recirculation pump(s), which can be low pressure but high flow pumps.

The pressure created by the RO feed pump and a RO concentrate flow restrictor 2181 can control the flow rate of waste to the drain. To ensure that the restriction does not become fouled or plugged, the flow through the RO concentrate flow restrictor can be periodically reversed by actuating valves 180. In addition, to improve filter life and performance, recirculation pumps can be used to increase fluid flow rate in the RO filter housings. This increase in flow rate can serve to reduce a boundary layer effect that can occur near the surface of RO filters where water near the filter membrane may not flow. The boundary layer can create an area with a higher concentration of total dissolved solids that can build up over the surface of the RO filter and may collect and foul the RO filter.

The RO filtration subsystem can include on or more conductivity sensors 196 configured to measure the conductivity of water flowing through the subsystem to measure solute clearance, or per, pressure sensors 198 configured to monitor fluid pressures, and air separators 187 configured to separate and remove air and air bubbles from the fluid. Additionally, the RO filtration subsystem can include a variety of valves 180, including check valves, and fluid pumps for controlling flow through the RO filters and on to the pasteurization subsystem, back through the RO filtration subsystem for further filtration, or to the drain. Water can flow from the RO filtration subsystem to the pasteurization subsystem, described next.

Figure 13:
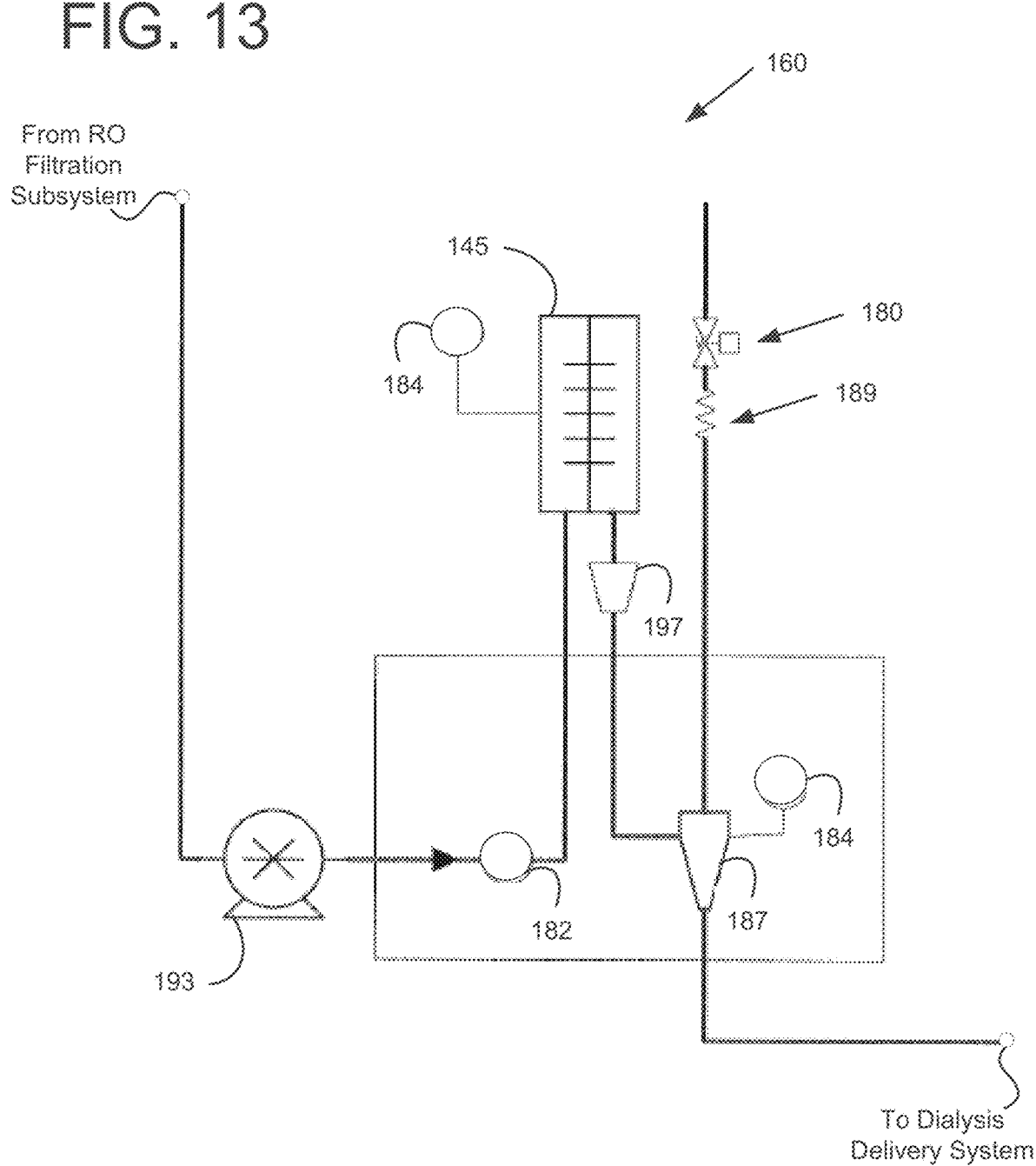
FIG. 13 illustrates one embodiment of a pasteurization subsystem of the water preparation system.

FIG. 13 illustrates one embodiment of a pasteurization subsystem 160 of the water preparation system. The pasteurization subsystem can be configured to minimize patient exposure to microbiological contamination by heating the fluid to eliminate microbiological contamination and endotoxins from the system. The pasteurization subsystem can include a heat exchanger (HEX) 145 configured to heat water to pasteurization temperature, allow the water to dwell at the high temperature, and then cool the water back to a safe temperature for the creation of dialysate.

In some embodiments, the HEX 145 can heat water received by the pasteurization subsystem to a temperature of approximately 148 degrees Celsius. The heated water can be held in a dwell chamber of the HEX for a time period sufficient to eliminate and kill bacteria and denature endotoxins. Endotoxins can be described as the carcasses of dead bacteria, characterized by long lipid chains. During water and dialysate preparation, endotoxins can be monitored along with bacteria to judge the purity of the dialysate. Endotoxins in dialysate can cause an undesirable inflammatory response in users. Therefore, it is desirable to minimize the levels of endotoxin in the dialysate. Endotoxins are not readily trapped by the pore size of typical ultrafilters. Instead, the endotoxins are stopped by ultrafilters through surface adsorption which can become saturated with endotoxins to the point that additional endotoxin will start to pass through. Heating endotoxins in superheated water to temperatures as low as 130 degrees C. have been demonstrated to denature endotoxins but the required dwell time is very long (many minutes). At these elevated temperatures, where the water remains in the liquid phase, water which is typically considered a polar solvent and begins to behave like a non-polar solvent to denature the lipid chains of the endotoxin. As the temperature increases to 220 degrees C. or higher, the denaturing of endotoxins occurs in seconds. The HEX of the present disclosure can run at 220 degrees C. or higher while maintaining a pressure (approximately 340 psi for 220 degrees C., but the HEX can withstand pressures of over 1000 psi) that keeps the water in liquid form. In one embodiment, a preferred temperature and pressure range of the HEX is 180-220 degrees C. and 145-340 psi. The water can then be cooled as it exits the dwell chamber. The HEX 145 is a self-contained counterflow heat exchanger that simultaneously heats incoming water and cools outgoing water to reduce energy consumption.

The pasteurization subsystem can include a HEX pump 193 configured to maintain a fluid pressure in the fluid line, to prevent the water from boiling. After the water passes through the HEX 145, a water regulator 197 can reduce the pressure of the water for use in the dialysis delivery system. One or more pressure sensors 182 or temperature sensors 184 can be included for measuring pressure and temperature, respectively, of the water flowing through the pasteurization subsystem. Furthermore, an air separator 187 can further remove air and air bubbles from the water. In one embodiment, a flow restrictor 189 and valve 180 can be used to limit water dumped to the drain when the HEX 145 is heating up. Once the water has passed through the pasteurization subsystem, it has traveled through the entire water purification system and is clean and pure enough to be used in dialysate preparation and delivery by the dialysis delivery system.

Figure 14:
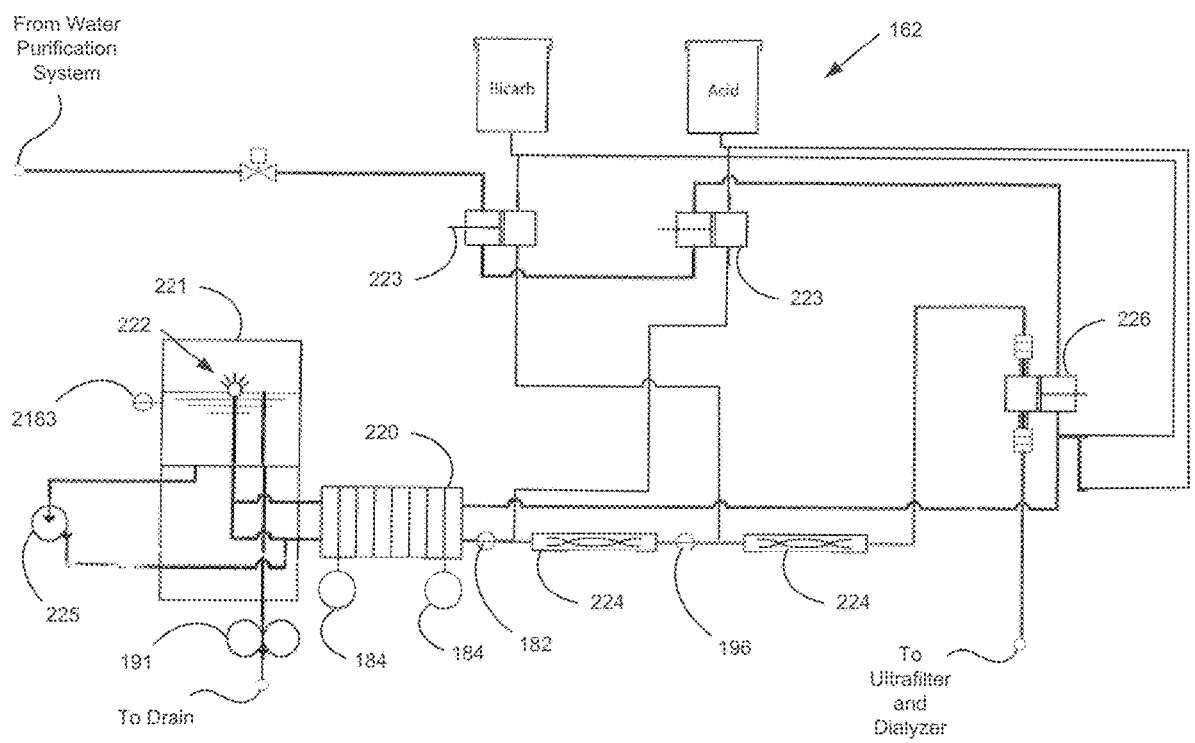
FIG. 14 illustrates a schematic of a mixing subsystem of the dialysis delivery system.

FIG. 14 illustrates a schematic of a mixing subsystem 162 of the dialysis delivery system. Purified water from the water purification system can be routed into the dialysis delivery system, where it can flow through heater 220 in preparation for final de-aeration in de-aeration chamber 221. In one embodiment, water flowing into the heater 220 can be approximately 43-47 degrees C., and the heater can heat the water up to 50 degrees C. or higher. The de-aeration chamber can be, for example, a spray chamber including a pump sprayer 222. During de-aeration, spray chamber recirculation pump 225 draws fluid at a high flow rate from the bottom of the de-aeration chamber. Heated water entering from the heater 220 then enters the de-aeration chamber above the fluid level through a pump sprayer 222. The temperature of the water as it enters and exits the heater can be monitored with temperature sensors 184. This restrictive spray head in combination with the high flow rate of the spray chamber recirculation pump 225 creates a vacuum in the de-aeration chamber ranging from −7 psig to −11 psig. The vacuum pressure and heat combine to effectively de-aerate the incoming water. As air collects in the top of the de-aeration chamber and the water level drops below level sensor 2183, the degas pump 191 can turn on or run faster to remove the collected air from the top of the de-aeration chamber. The degas pump 191 can remove a combination of air and liquid from the de-aeration chamber.

Figure 15:
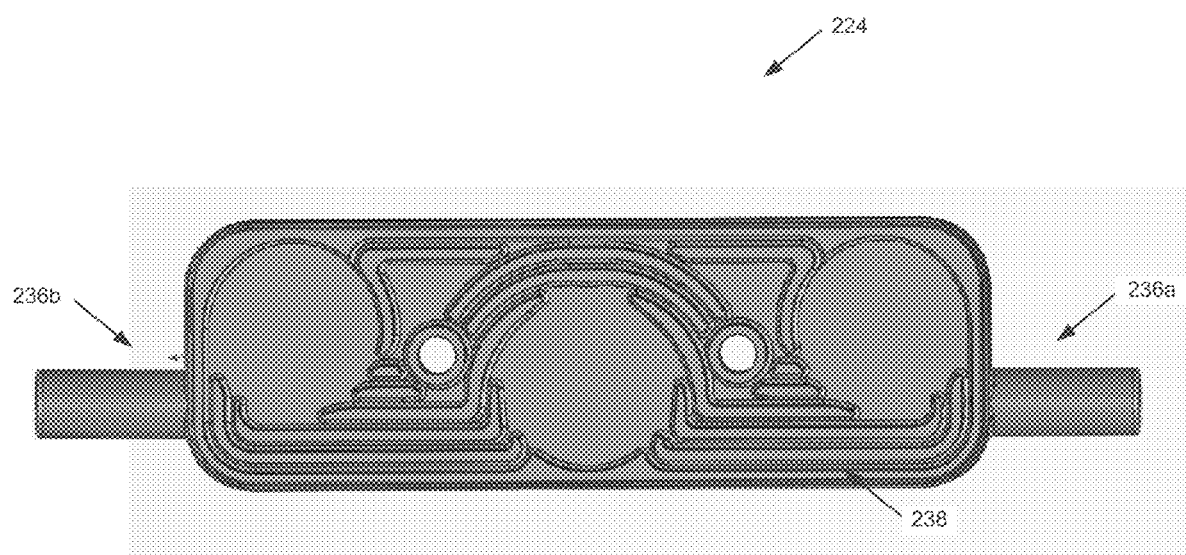
FIG. 15 shows one embodiment of a mixing chamber.

After de-aeration and subsequent cooling with the heater 220 to approximately body temperature, acid and bicarbonate concentrates can be volumetrically proportioned into the fluid path by way of concentrate pumps 223 in order to reach the desired dialysate composition. The water and concentrates can be mixed in a series of mixing chambers 224 that utilize a time delay or volumetric mixing instead of in-line mixing to smooth the introduction of fluids. FIG. 15 shows one embodiment of a mixing chamber 224, which can include an inlet portion 236a and an outlet portion 236b. The mixing chamber can include a plurality of channels 238 connecting the inlet portion to the outlet portion. The channels can be arranged so that some of the channels include longer paths from the inlet portion to the outlet portion than other channels. Thus, fluid traveling through the channels of the mixing chamber can be separated and divided along the varying channel lengths before being recombined to achieve more complete mixing of "lumpy" incoming fluid by the time it exits the mixing chamber.

In one embodiment, the concentrate pumps can run at an elevated rate to push out any air bubbles in the pumping mechanism (e.g., can run at upwards of 30 ml/min compared to ~7 ml/min during normal operation). Once the dialysate is mixed, a dialysate pump 226 can control the flow of dialysate through the dialysis delivery system. The mixing subsystem 162 can include various pressure sensors 182, temperature sensors 184, and conductivity sensors 196 to monitor the fluid during the dialysate preparation. The conductivity sensors can be used to measure the fluid ionic properties to confirm that the composition is correct.

The flow path within the dialysis delivery system can include one or more bypass or circulation routes that permit circulation of cleaning and/or sterilization fluid through the flow path. The circulation route may be an open flow loop wherein fluid flowing through the circulation route can be dischargeable from the system after use. In another embodiment, the circulation route may be a closed flow loop wherein fluid flowing through the circulation route is not dischargeable from the system.

Figure 16:
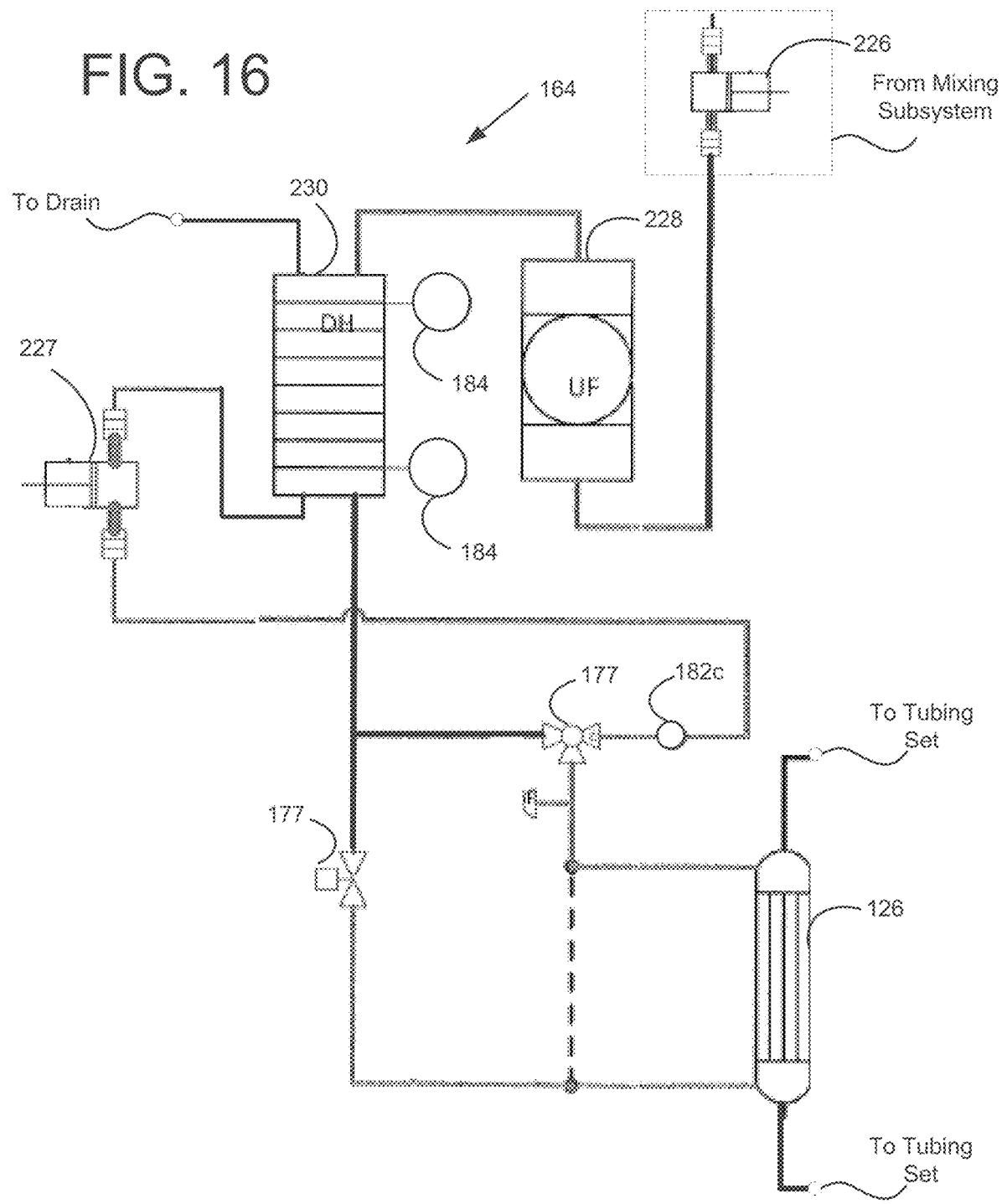
FIG. 16 illustrates an ultrafiltration subsystem of the dialysis delivery system which can receive the prepared dialysate from the mixing subsystem.

FIG. 16 illustrates an ultrafiltration subsystem 164 of the dialysis delivery system which can receive the prepared dialysate from the mixing subsystem. The ultrafiltration subsystem is configured to receive prepared dialysate from the mixing subsystem 162. Dialysate pump 226 and used dialysate pump 227 can be operated to control the flow of dialysate through the ultrafiltration subsystem. The pumps 226 and 227 can control the flow of dialysate to pass through an ultrafilter 228 and a dialysate heater 230 before entering dialyzer 126. Temperature sensors 184 can measure the temperature of the dialysate before and after passing through the dialysate heater 230. The dialysate heater can be user configurable to heat the dialysate based on the user's preference, typically between 35-39 degrees C. After passing through the dialyzer, the used dialysate can flow through a used dialysate pump 230 and back through the dialysate heater 228 before returning to drain. In one embodiment, the degas pump from FIG. 14 can be used to wet the back of the used dialysate pump 227. The ultrafiltration subsystem can include one or more actuators or valves 177 that can be controlled to allow dialysate to pass through the dialyzer 126, or alternatively, to prevent dialysate from passing through the dialyzer in a "bypass mode". A pressure sensor 182c disposed between the dialysate pump 226 and the used dialysate pump 227 can be configured to measure a pressure of the dialysate between the pumps when dialysate is prevented from passing through the dialyzer in the "bypass mode".

Figure 17:
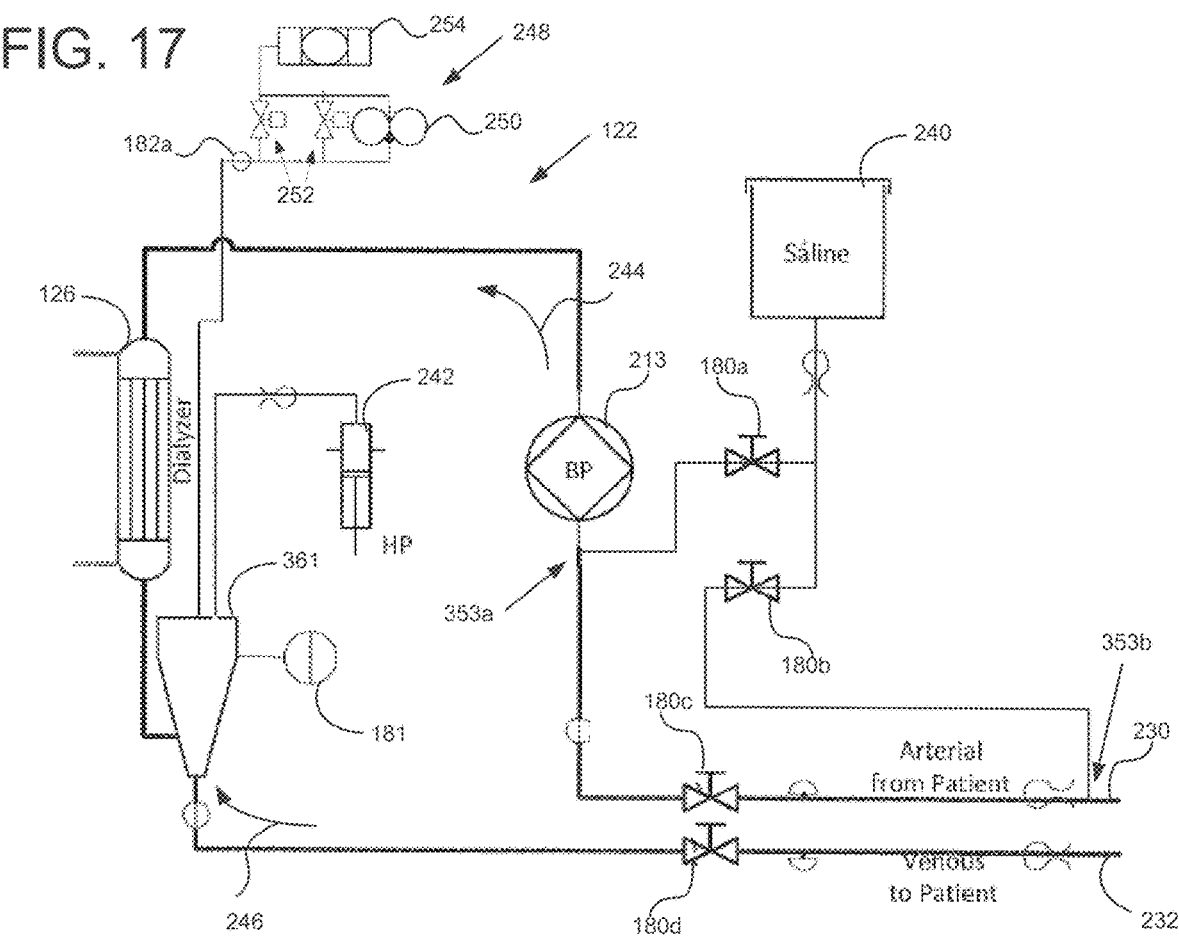
FIG. 17 shows a schematic diagram illustrating the flow of saline through tubing set during blood return to the user.

FIG. 17 illustrates a blood circuit subsystem 166 which is configured to pull blood from the patient and create a flow of blood through the dialyzer during dialysis therapy to pass fluid from the blood-side of the dialyzer to the dialysate-side of the dialyzer or vice versa. As described above, the blood circuit subsystem 166 can include, among other features described herein, the tubing set 122, blood pump 213, pinch clamps 180a-d, venous drip chamber 361, venous level sensor(s) 181, arterial line 230, and venous line 232, saline source 240, and heparin pump 242. The blood pump 213 can be controlled to operate in first and second modes of operation. During dialysis therapy, the blood pump 213 can be operated in a first operating mode in which the pump pulls blood from the patient through arterial line 230, flows through the tubing set in the direction of arrow 244, flows through the dialyzer 126, flows through the venous drip chamber 361, and is returned to the patient through venous line 232. The blood pump can also be operated in a second operating mode in which the pump direction is reversed to cause fluid in the lines to flow in the direction of arrow 246 (for example, during a priming sequence as described above.

The blood circuit subsystem can also include a venting circuit 248 adapted to automatically control the fluid level in venous level chamber 361, as described above. The venting circuit can include a pressure compensating pump 250, one or more venting valves 252, and an air filter 254. The venous pressure sensor 182a of the system can also be located in the venting circuit 248. During dialysis therapy, the venous level sensor(s) 181 can monitor a fluid level of blood in the venous drip chamber 361. The electronic controller can receive the fluid level information from the sensor(s) and automatically maintaining the fluid level of the blood in the venous drip chamber by pumping or venting air out of the venous drip chamber with pressure compensating pump 250 and/or venting valves 252 if sensor(s) detect the fluid level dropping below a lower threshold, and by pumping air into the venous drip chamber if the sensor(s) detect the fluid level rising above an upper threshold.

Still referring to FIG. 17, a method of returning blood in the tubing set to the patient after dialysis therapy will be described. First, the user can clamp the line on their arterial needle (not shown in diagram) at the point where the arterial line 230 enters their body. This clamp can be located in between saline connection 353b and the user's body. The user can then confirm ACLMP is open, which is another clamp on the arterial line distal to the saline connection 353b. Next, the electronic controller of the dialysis system can open pinch clamps 180b and 180c, and close pinch clamp 180a. Next, the electronic controller can direct blood pump 213 to operate in the "forward direction" to draw saline from the saline source (e.g., a saline bag) into the arterial line 230 at saline connection 353b through pinch clamp 180b, which is very close to where the arterial line connects to the patient. The blood pump can operate for a specified time, or can run until a predetermined volume of saline (e.g., 300-600 ml) is drawn into the tubing set, to return the blood in the tubing set and dialyzer into the patient through venous line 232. In some embodiments, the blood return process can be manually stopped based on the color of the saline in the tubing set (i.e., stopping the blood pump when the color of the saline becomes clear or a light-pink color).

The dialysate pump and used dialysate pump described above can be part of an electronic circuit in communication with the electronic controller of the dialysis system to achieve a controlled ultrafiltration rate, and can also be adjusted to precisely control the addition or removal of fluid to or from the patient.

The dialysate pump and used dialysate pump can be controlled with a high degree of precision to achieve dynamic balancing, periodic balancing, and continuous correction. Referring to FIGS. 16-17, dialysate pump 226 and used dialysate pump 227 can be configured to pump dialysate through the dialysis delivery system. The dialysate pump can be controlled to push the dialysate through the ultrafilter and the dialysate heater to get heated.

To calibrate the flow of the system, the system can be controlled to enter a bypass mode in which valves 177 are actuated to prevent dialysate flow through the dialyzer. This isolates the patient tubing set on the blood side of the dialyzer from the dialysate flow and creates a closed system for dialysate flow that will not allow ultrafiltration. Whenever the system is in bypass the used dialysate pump can be servoed to maintain constant pressure as measured by pressure sensor 182c, which is positioned between the dialysate pump 226 and used dialysate pump 227. The pump speed of the used dialysate can be adjusted while the pump speed of the dialysate pump is maintained at a constant speed until the pressure measured by pressure sensor 182c stabilizes. Once the pressure is stabilized, the pump speed of the used dialysate pump vs the pump speed of the dialysate pump can be recorded as the pump speed ratio that results in zero ultrafiltration. When the systems exits bypass and returns to dialysis therapy, the used dialysate pump speed can be adjusted based on the desired ultrafiltration rate.

When dialyzer is bypassed, pressure measurements of the dialysate can be made independent of influences or pressures from the blood-side of the dialyzer (e.g., isolated from the blood tubing set). When the dialysate and used dialysate pumps operate at the same rate there is no pressure change at pressure sensor 182c positioned between the two pumps, so there is no flow imbalance between the pumps. However, if the dialysate and used dialysate pumps operate at different rates then a flow imbalance is created between the pumps, and a pressure change representing this flow imbalance can be measured at pressure sensor 182c. In some embodiments, the flow imbalance can be controlled based on the pump strokes of the respective pumps. In other embodiments, the flow imbalance can be controlled based on lookup tables that determine the optimal pump speeds based on the measured venous pressure. The electronic controller of the system can be configured to automatically control the flow of fluid across the dialyzer (i.e., ultrafiltration) by adjusting a pump speed of the used dialysate pump 227 with respect to dialysate pump 226 (or alternatively, of the dialysate pump 226 with respect to used dialysate pump 227) to create a flow imbalance between the dialysate-side and blood-side of the dialyzer. When a flow imbalance is created on the dialysate-side of the dialyzer by operating the pumps 226 and 227 at different speeds, then fluid can flow across the dialyzer membranes from the blood-side to the dialysate-side, and vice versa, to equalize that flow imbalance.

The pump speeds of the dialysate pump 226 and used dialysate pump 227 can be locked in by the system based on a desired rate of ultrafiltration, and valve 180 can be opened for normal operation during dialysis therapy. During therapy, the system can continue to monitor venous pressure on user side at pressure sensor 182a. If the venous pressure changes (e.g., greater than 30mm-Hg mercury in change), the system can be configured to automatically rebalance the pumps with the same technique described above. This allows the pumps to be balanced to achieve the desired amount of fluid transfer through the dialyzer, or alternatively, to achieve no fluid transfer through the dialyzer. In one specific embodiment, the system can detect changes in the venous pressure of the user and automatically adjust the speed of the used dialysate pump 227 based on a look-up table of speeds against venous pressure to maintain ultrafiltration balance in the user. Once the system has been calibrated, the used dialysate pump speed can be modulated to adjust the rate of fluid removal from the patient. In some embodiments, a pump speed of the used dialysate pump can be alternatively increased or decreased relative to the dialysate pump to enable hemodiafiltration (e.g., pushing/pulling fluid onto the patient).

As described above, the water purification system and the dialysate delivery system can both include a variety of pumps, valves, sensors, air separators, air sensors, heat exchangers, and other safety features. All of these features can be controlled electronically and automatically by the electronic controller of the dialysis system.

What is claimed is:

1. A method of controlling a fluid level in a venous drip chamber of a dialysis system, the dialysis system having a blood pump and an air pump, the method comprising the steps of:
    operating the blood pump in a first operating mode to flow saline in a first direction from a saline source, into a patient tubing set, into a venous drip chamber through a first port disposed at a bottom portion of the venous drip chamber, out of the venous drip chamber through a second port disposed at the bottom portion of the venous drip chamber, and into a dialyzer;
    monitoring a saline fluid level in the venous drip chamber with at least one sensor;
    operating the blood pump in a second operating mode to move blood in a second direction opposite to the first direction through a continuous pathway of the dialysis system, comprising moving blood with the blood pump from a patient into the patient tubing set via an arterial access point, moving blood with the blood pump through the dialyzer, moving blood with the blood pump into the venous drip chamber through the second port, moving blood with the blood pump out of the venous drip chamber through the first port, and moving blood out of the patient tubing set and back into the patient via a venous access point;
    monitoring a blood fluid level in the venous drip chamber with the at least one sensor;
    raising the blood fluid level in the venous drip chamber by automatically pumping air out of the venous drip chamber with the air pump if the fluid level is below a level detected by the at least one sensor; and
    lowering the blood fluid level by automatically pumping air into the venous drip chamber with the air pump if the blood fluid level is above a level detected by the at least one sensor.

2. The method of claim 1 wherein the at least one sensor comprises at least one ultrasonic sensor.

3. The method of claim 1 wherein the at least one sensor comprises at least one optical sensor.

4. The method of claim 1 wherein the at least one sensor comprises at least one capacitive sensor.

5. The method of claim 1, wherein the arterial access point comprises an arterial needle and the venous access point comprises a venous needle.

6. The method of claim 1, wherein the arterial access point comprises an arterial catheter and the venous access point comprises a venous catheter.

7. A method of controlling a fluid level in a venous drip chamber of a dialysis system, the dialysis system having a blood pump and an air pump, the method comprising the steps of:
    operating the blood pump in a first operating mode to flow saline in a first direction from a saline source, into a patient tubing set, into a venous drip chamber through a first port disposed at a bottom portion of the venous drip chamber, out of the venous drip chamber through a second port disposed at the bottom portion of the venous drip chamber, and into a dialyzer;
    monitoring a saline fluid level in the venous drip chamber with at least one sensor;
    operating the blood pump in a second operating mode to move blood with the blood pump in a second direction opposite to the first direction through a continuous pathway of the dialysis system, comprising moving blood with the blood pump from a patient into the patient tubing set via an arterial access point, moving blood with the blood pump through the dialyzer, moving blood with the blood pump into the venous drip chamber through the second port, moving blood with the blood pump out of the venous drip chamber through the first port, and moving blood out of the patient tubing set and back into the patient via a venous access point;
    monitoring a blood fluid level in the venous drip chamber with the at least one sensor; and
    automatically maintaining the blood fluid level in the venous drip chamber by pumping air out of the venous drip chamber with the air pump if the at least one sensor detects the blood fluid level dropping below a lower threshold and pumping air into the venous drip chamber with the air pump if the at least one sensor detects the blood fluid level rising above an upper threshold.

8. The method of claim 7 wherein the at least one sensor comprises at least one ultrasonic sensor.

9. The method of claim 7 wherein the at least one sensor comprises at least one optical sensor.

10. The method of claim 7 wherein the at least one sensor comprises at least one capacitive sensor.

11. The method of claim 7 wherein pumping air out of the venous drip chamber raises the blood fluid level in the venous drip chamber above the lower threshold.

12. The method of claim 7 wherein pumping air into the venous drip chamber lowers the blood fluid level in the venous drip chamber below the upper threshold.

13. The method of claim 7, wherein the arterial access point comprises an arterial needle and the venous access point comprises a venous needle.

14. The method of claim 7, wherein the arterial access point comprises an arterial catheter and the venous access point comprises a venous catheter.

15. A method of controlling a fluid level in a venous drip chamber of a dialysis system, the dialysis system having a blood pump and an air pump, the method comprising the steps of:

operating the blood pump in a first operating mode to flow saline in a first direction from a saline source, into a patient tubing set, into a venous drip chamber through a first port disposed at a bottom portion of the venous drip chamber, out of the venous drip chamber through a second port disposed at the bottom portion of the venous drip chamber, and into a dialyzer;

operating the blood pump in a second operating mode to move blood with the blood pump in a second direction opposite to the first direction through a continuous pathway of the dialysis system, comprising moving blood with the blood pump from a patient into the patient tubing set via an arterial access point, moving blood with the blood pump through the dialyzer, moving blood with the blood pump into the venous drip chamber through the second port, moving blood with the blood pump out of the venous drip chamber through the first port, and moving blood out of the patient tubing set and back into the patient via a venous access point;

monitoring a blood fluid level in the venous drip chamber with at least one sensor;

automatically pumping air out of the venous drip chamber with the air pump to raise the blood fluid level if the monitored fluid level is below a level detected by the at least one sensor; and automatically pumping air into the venous drip chamber with the air pump to lower the blood fluid level if the monitored fluid level is above a level detected by the at least one sensor.

16. The method of claim 15, wherein the arterial access point comprises an arterial needle and the venous access point comprises a venous needle.

17. The method of claim 15, wherein the arterial access point comprises an arterial catheter and the venous access point comprises a venous catheter.

\* \* \* \* \*